(12) United States Patent
Begley et al.

(10) Patent No.: US 6,194,132 B1
(45) Date of Patent: *Feb. 27, 2001

(54) PHOTOGRAPHIC ELEMENT, COMPOUND, AND PROCESS

(75) Inventors: William J. Begley, Webster; Frank D. Coms, Fairport; Gary M. Russo, Rochester, all of NY (US)

(73) Assignee: Eastman Kodak Company, Rochester, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/473,632

(22) Filed: Dec. 28, 1999

(51) Int. Cl.⁷ .............................. G03C 1/08; G03C 7/26; G03C 7/32
(52) U.S. Cl. .................. 430/553; 430/552; 430/384; 430/385
(58) Field of Search ................ 430/543, 552, 430/553, 384, 385

(56) References Cited

U.S. PATENT DOCUMENTS

| | | |
|---|---|---|
| 4,609,619 | 9/1986 | Katoh et al. . |
| 4,775,616 | 10/1988 | Kilminster et al. . |
| 4,849,328 | 7/1989 | Hoke et al. . |
| 5,008,180 | 4/1991 | Merkel et al. . |
| 5,045,442 | 9/1991 | Hoke . |
| 5,183,729 | 2/1993 | Naito et al. . |
| 5,378,596 | 1/1995 | Naruse et al. . |
| 5,674,666 * | 10/1997 | Lau et al. ............... 430/384 |
| 5,681,690 | 10/1997 | Tang et al. . |
| 5,686,235 | 11/1997 | Lau et al. . |
| 5,888,716 * | 10/1999 | Edwards et al. ............... 430/549 |
| 5,962,198 * | 10/1999 | Lau et al. ............... 430/553 |
| 6,048,674 * | 10/1999 | McInerney et al. ............... 430/384 |
| 6,110,658 * | 8/2000 | Honan et al. ............... 430/552 |

FOREIGN PATENT DOCUMENTS

| | | |
|---|---|---|
| 59-111645 | 6/1984 | (JP) . |
| 1253-742 | 10/1989 | (JP) . |
| 2035-450 | 2/1990 | (JP) . |
| 04163448 | 6/1992 | (JP) . |
| 04212152 | 8/1992 | (JP) . |

* cited by examiner

Primary Examiner—Geraldine Letscher
(74) Attorney, Agent, or Firm—Arthur E. Kluegel

(57) ABSTRACT

Disclosed is a photographic element comprising a light-sensitive silver halide emulsion layer having associated therewith a cyan coupler having the formula:

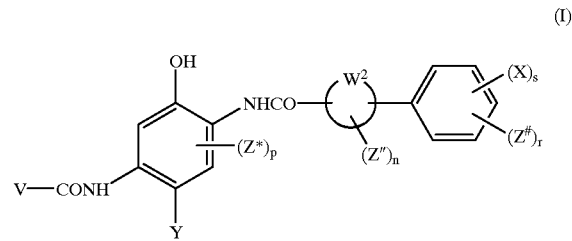

(I)

wherein:

V is a sulfone or sulfoxide containing group;

Y is H or a coupling-off group;

$W^2$ represents the atoms necessary to complete a carbocyclic or heterocyclic ring group;

each $Z''$, $Z^*$ and $Z^\#$ is an independently selected substituent group where n and r are independently 0 to 4 and p is 0 to 2; and X is a halogen atom, and s is 1 to 5;

provided that the combined sum of the aliphatic carbon atoms in V, all $Z''$, all $Z^\#$, and all $Z^*$ is at least 8. The element exhibits improved cyan dye stability.

23 Claims, No Drawings

PHOTOGRAPHIC ELEMENT, COMPOUND, AND PROCESS

FIELD OF THE INVENTION

This invention relates to a silver halide photographic element containing a phenolic cyan dye-forming coupler bearing a carbonamido group in the 2-position and a carbonamido substituent bearing a sulfone group in the 5-position.

BACKGROUND OF THE INVENTION

In silver halide based color photography, a typical photographic element contains multiple layers of light-sensitive photographic silver halide emulsions coated on a support with one or more of these layers being spectrally sensitized to each of blue light, green light and red light. The blue, green, and red light-sensitive layers typically contain yellow, magenta, and cyan dye-forming couplers, respectively. After exposure to light, color development is accomplished by immersing the exposed material in an aqueous alkali solution containing an aromatic primary amine color-developing agent. The dye-forming couplers are selected so as to react with the oxidized color developing agent to provide yellow, magenta and cyan dyes in the so called subtractive color process to reproduce their complementary colors, blue, green and red as in the original image.

The important features for selecting the dye-forming coupler include, efficient reaction with oxidized color developing agent, thus minimizing the necessary amounts of coupler and silver halide in the photographic element; the formation of dyes with hues appropriate for the photographic use of interest, for color photographic paper applications this requires that dyes have low unwanted side absorption leading to good color reproduction in the photographic print; minimization of image dye loss contributing to improved image permanence under both ambient illumination and conventional storage conditions; and in addition the selected dye-forming coupler must exhibit good solubility in coupler solvents, provide good dispersibility in gelatin and remain stable during handling and manipulation for maximum efficiency in manufacturing processes.

In recent years, a great deal of study has been conducted to improve dye-forming couplers for silver halide photosensitive materials in terms of improved color reproducibility and image dye stability. However, further improvements are needed, particularly in the area of cyan couplers. In general, cyan dyes are formed from naphthols and phenols as described, for example, in U.S. Pat. Nos. 2,367,351, 2,423,730, 2,474,293, 2,772,161, 2,772,162, 2,895,826, 2,920,961, 3,002,836, 3,466,622, 3,476,563, 3,552,962, 3,758,308, 3,779,763, 3,839,044, 3,880,661, 3,998,642, 4,333,999, 4,990,436, 4,960,685, and 5,476,757; in French patents 1,478,188 and 1,479,043; and in British patent 2,070,000. These types of couplers can be used either by being incorporated in the photographic silver halide emulsion layers or externally in the processing baths. In the former case the couplers must have ballast substituents built into the molecule to prevent the couplers from migrating from one layer into another. Although these couplers have been used extensively in color photographic film and paper products, the dyes derived from them still suffer from poor stability to heat, humidity or light, low coupling efficiency or optical density, and in particular from undesirable blue and green absorptions which cause considerable reduction in color reproduction and color saturation.

Cyan couplers which have been recently proposed to overcome some of these problems are 2,5-diacylaminophenols containing a sulfone, sulfonamido or sulfate moiety in the ballasts at the 5-position, as disclosed in U.S. Pat. Nos. 4,609,619, 4,775,616, 4,849,328, 5,008,180, 5,045,442, and 5,183,729; and Japanese patent applications JP02035450 A2, JP01253742 A2, JP04163448 A2, JP04212152 A2, and JP05204110 A2. Even though cyan image dyes formed from these couplers allege in various instances improved stability to heat and humidity, enhanced optical density and resistance to reduction by ferrous ions in the bleach bath, the dye absorption maxima ($\lambda$max) are too hypsochromically shifted (that is, shifted to the blue end of the visible spectrum) and the absorption spectra are too broad with considerable amounts of undesirable blue and green absorptions and often lack sufficient stability toward light fading. Thus, these couplers are not acceptable for use in color papers and print applications.

The hue of a dye is a function of both the shape and the position of its spectral absorption band. Traditionally, the cyan dyes used in color photographic papers have had nearly symmetrical absorption bands centered in the region of 620 to 680 nm, typically 630 to 660 nm. Such dyes have rather large amounts of unwanted absorption in the green and blue regions of the spectrum.

More desirable would be a dye whose absorption band is asymmetrical in nature and biased towards the green region, that is, with a steep slope on the short wavelength side. The half-bandwidth on the short side of the curve, also called the left half-bandwidth or LBW, is desirably narrowed. Such a dye would suitably peak at a shorter wavelength than a dye with symmetrical absorption band, but the exact position of the desired peak depends on several factors including the degree of asymmetry and the shapes and positions of the absorption bands of the magenta and yellow dyes with which it is associated.

Recently, Lau et al., in U.S. Pat. No. 5,686,235, describe a particular class of cyan dye-forming coupler that has been shown to improve thermal stability and hue, particularly, with decreased absorption in side bands and an absorption band that is asymmetrical in nature. The couplers disclosed as suitable contain a sulfone group bonded to the 2-position of an acetamido group at the 5-position of the phenolic ring and contain a phenylcarbonamido group in the 2-position of the phenolic ring. Other related patents are U.S. Pat. Nos. 5,047,314, 5,047,315, 5,057,408, and 5,162,197.

Although the coupler of Lau et al. provides an advantageous spectra, it is desirable to discover alternative phenolic structures that will accomplish the same result and that may provide other desirable features. Chemical variations may enable advances in the ability to better select the desired curve shape and wavelength of maximum absorption and other properties such as coupler and dye light and dark stability, reactivity etc.

Japanese published application 59-111,645 suggests certain phenolic couplers having an $\alpha$-sulfonyl substituent in a 5-carbonamido substituent that forms a dye having a maximum absorption at "about 660 nm" with examples of 657–660 nm. It appears that the spectral curve of the disclosed dyes exhibit the usual broad absorption band but that the curve has been shifted to the long wavelength side in order to reduce the unwanted absorption on the short wavelength side. The disclosed compounds do not provide the desired narrow LBW and shorter wavelength of maximum absorption.

In spite of the ongoing efforts to discover coupler that produce dyes having advantageous absorption properties, such dyes, even if obtained, will have limited utility if the formed dyes are not sufficiently stable.

The problem to be solved is to provide an alternative photographic element, compound, and process, employing a cyan dye-forming phenolic coupler which forms a dye having improved stability.

SUMMARY OF THE INVENTION

The invention provides a photographic element comprising a light-sensitive silver halide emulsion layer having associated therewith a cyan coupler having the formula:

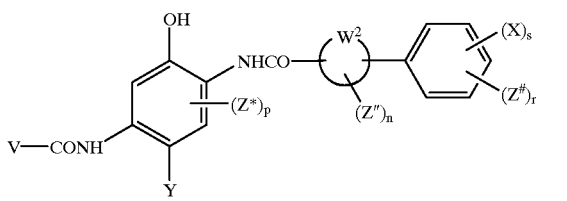

(I)

wherein:
- V is a sulfone or sulfoxide containing group;
- Y is H or a coupling-off group;
- $W^2$ represents the atoms necessary to complete a carbocyclic or heterocyclic ring group;
- each Z", $Z^*$ and $Z^\#$ is an independently selected substituent group where n and r are independently 0 to 4 and p is 0 to 2; and
- X is a halogen atom, and s is 1 to 5;
- provided that the combined sum of the aliphatic carbon atoms in V, all Z", all $Z^\#$, and all $Z^*$ is at least 8.

The invention also provides a coupler of formula (I) and an imaging method employing the element. The cyan dye formed in the element of the invention exhibits improved dye stability, particularly when the processed element is exposed to light.

DETAILED DESCRIPTION OF THE INVENTION

The invention may be generally described as summarized above.

The following limitations apply to formulas (I), (II), (III) and (IV) as appropriate:
- V represents a group comprising a sulfone or sulfoxide group. Preferably the group comprises a sulfone group and most preferably an aromatic sulfone group such as a phenylsulfone group.
- Y is H or a coupling-off group. Coupling-off groups are more fully described hereinafter. Typically, Y is H, halogen such as chloro, phenoxy, or alkoxy.
- L is any divalent linking group suitable for connecting the carbonamido group to the sulfur atom of V. It may, for example, represent a substituted or unsubstituted alkyl or aromatic group and may include a heteroatom, and it may comprise a combination of the foregoing.
- $R_1$ and $R_2$ are independently H or an alkyl group of 1 to 5 carbon atoms. Other groups and alkyl groups of longer chain length diminish the hue advantage. Desirably, one of $R_1$ and $R_2$ is hydrogen and the other is an alkyl group such as ethyl. Both may be hydrogen or both may be alkyl. It is also possible that the employed alkyl group is substituted to provide, for example, a perfluorinated substituent.
- Each Z', Z", $Z^*$, and $Z^\#$ is an independently selected substituent group where m, n, and r are independently 0 to 4 and p is 0 to 2. Suitable substituent groups are more fully described hereinafter. Typically p is 0. Z', Z", $Z^*$, and $Z^\#$ may be any substituent and, for example, may be independently selected from acyl, acyloxy, alkenyl, alkyl, alkoxy, aryl, aryloxy, carbamoyl, carbonamido, carboxy, cyano, halogen, heterocyclic, hydroxy, nitro, oxycarbonyl, oxysulfonyl, sulfamoyl, sulfonamido, sulfonyl, sulfoxide, thio, and ureido groups. Convenient substituents are alkyl, alkoxy, sulfonyl, sulfamoyl, nitro, and halogen groups. The total combined sum of the aliphatic carbon atoms in $R_1$, $R_2$, all Z', all Z", all $Z^\#$, and all $Z^*$ groups is at least 8.

$W^1$ and $W^2$ independently represent the atoms necessary to form a carbocyclic or heterocyclic ring group. Examples of suitable carbocyclic rings include cyclohexyl, phenyl and naphthyl with phenyl rings being most conveniently used. Suitable heterocyclic rings include those containing 5 or 6 ring members and at least one ring heteroatom. Heterocycles useful herein may be aromatic or non-aromatic and contain at least one atom of oxygen, nitrogen, sulfur, selenium, or tellurium. They can be fused with a carbocyclic ring or with another heterocycle. They can be attached to the coupler through any of the possible points of attachment on the heterocycle. It should be realized that multiple points of attachment are possible giving rise to alternative isomers for a single heterocycle. Examples of useful heterocyclic groups are benzimidazolyl, benzoselenazolyl, benzothiazolyl, benzoxazolyl, chromonyl, furyl, imidazolyl, indazolyl, indolyl, isoquinolyl, isothiazolyl, isoxazolyl, morpholinyl, oxadiazolyl, oxazolyl, picolinyl, piperidinyl, purinyl, pyradazinyl, pyranyl, pyrazinyl, pyrazolyl, pyridyl, pyrimidinyl, pyrrolyl, pyrrolidinyl, quinaldinyl, quinazolinyl, quinolyl, quinoxalinyl, selenazoyl, tellurazolyl, tetrazolyl, tetrahydrofuryl, thiadiazolyl, thiamoipholinyl, thiatriazolyl, thiazolyl, thienyl, thiophenyl, and triazolyl groups.

X is a halogen atom, and s is 1 to 5. s is conveniently 2 or 3 and the halogen selection is suitably chloro or bromo.

In one embodiment the coupler of formula (I) is represented by formula (II):

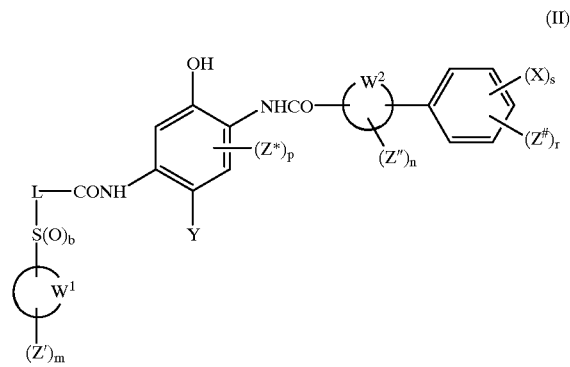

(II)

wherein:
- L is a linking group;
- b is 1 or 2;
- Y is H or a coupling-off group;
- each Z' is an independently selected substituent group where m is 0 to 4;
- $W^1$ represents the atoms necessary to complete a heterocyclic or carbocyclic ring group;

provided that the combined sum of the aliphatic carbon atoms in L, all Z', all Z" and all Z* is at least 8.

In another embodiment, the coupler of formula (II) is represented by formula (III):

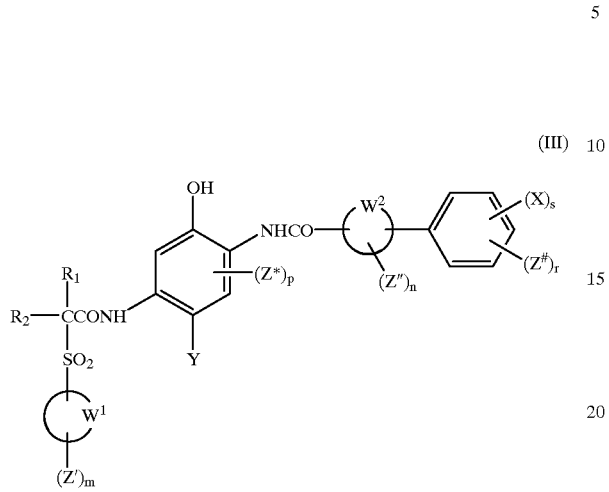

wherein:

R$_1$ and R$_2$ are independently H or an alkyl group of 1 to 5 carbon atoms;

provided that the combined sum of the aliphatic carbon atoms in R$_1$, R$_2$, all Z', all Z", all Z$^\#$ and all Z* is at least 8.

In a still further embodiment, the coupler of formula (III) is represented by formula (IV).

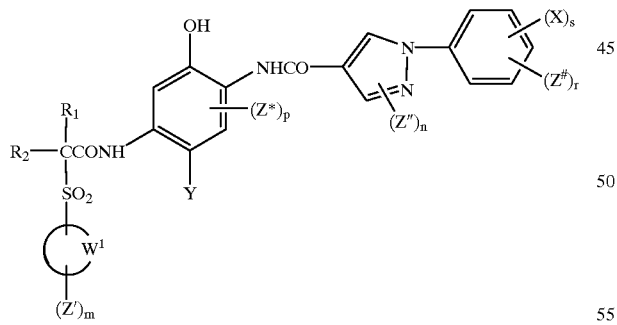

wherein n is 0 to 2.

Examples of suitable heterocycles are those based on a benzimidazole, benzotriazole, furan, imidazole, indazole, indole, isoquinoline, purine, pyrazole, pyridine, pyrimidine, pyrrole, quinoline, thiophene, 1,2,3-triazole, or 1,2,4-triazole ring group. Conveniently useful are the nitrogen-containing rings such as pyridine with the nitrogen in the 2-, 3-, or 4-position, as well as the various pyrimidine or pyrazole alternatives, as shown in the following coupler formulas.

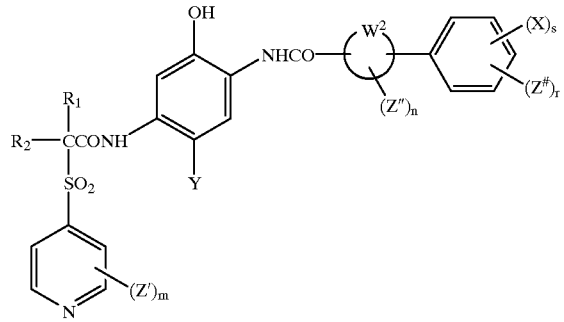

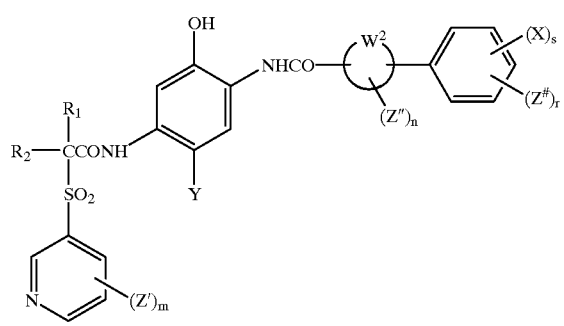

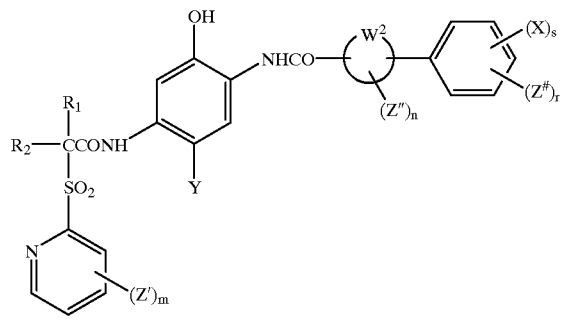

Typically, R$_1$ and R$_2$ contain only a few, if any, aliphatic carbon atoms and the rest of the aliphatic carbon atoms are located in Z', Z$^\#$, and/or Z". Often, the Z', Z$^\#$, or Z" group bears an aliphatic carbon number of 12 or more with 15 or 16 being not uncommon.

The following are examples of couplers useful in the invention.

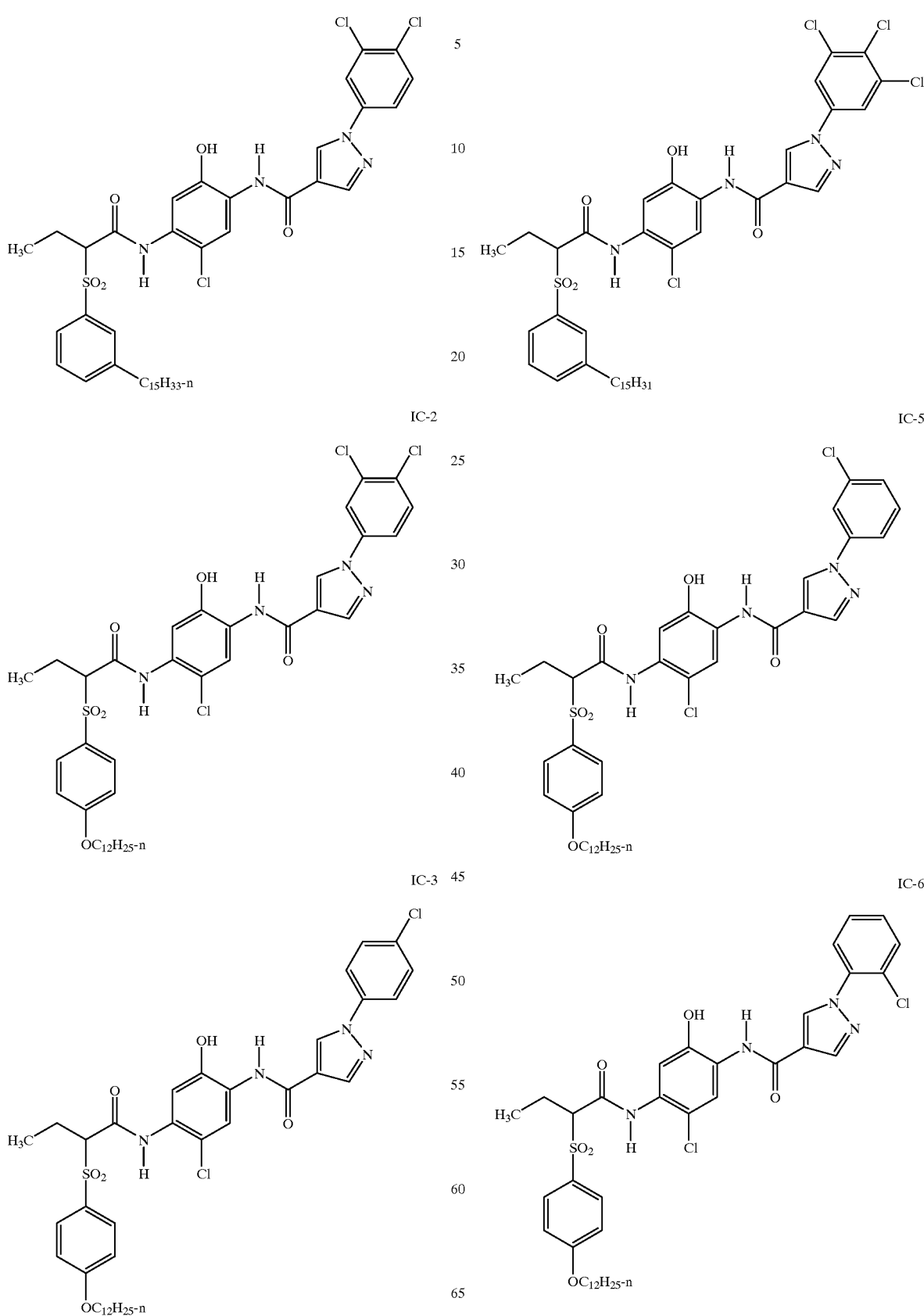

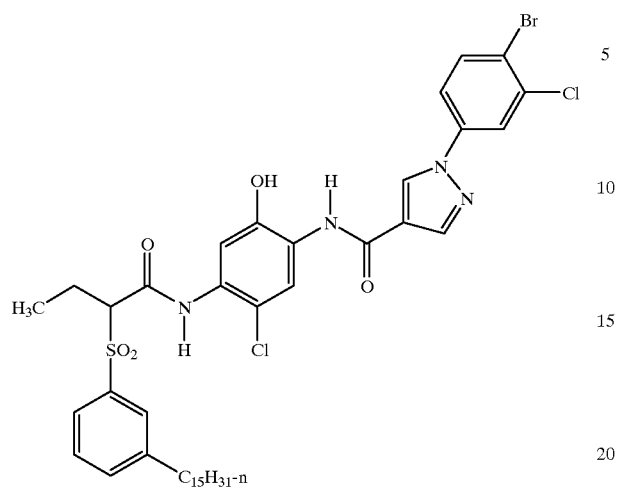
IC-7
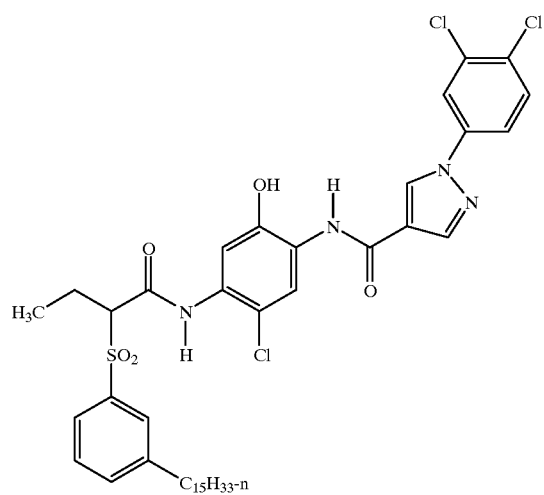
IC-8
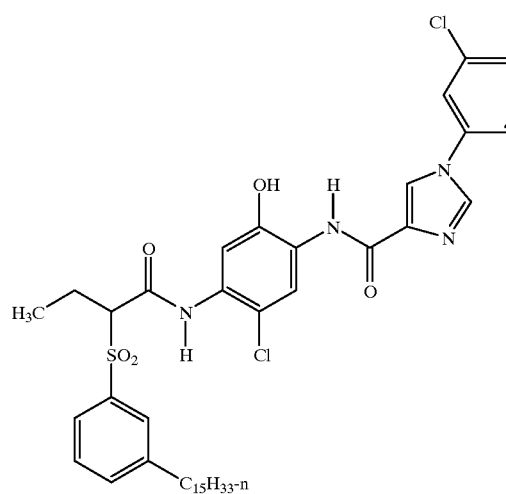
IC-9
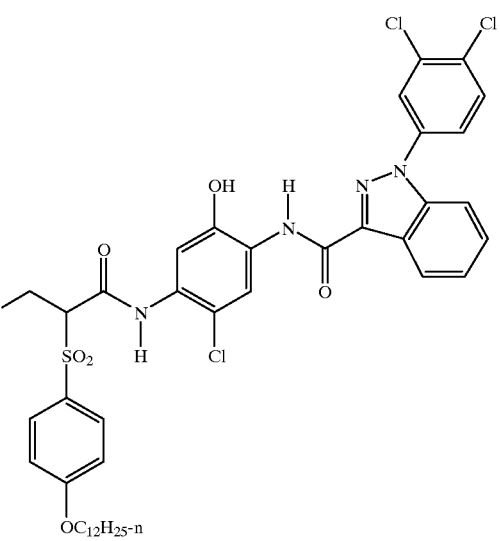
IC-10, IC-11, IC-12

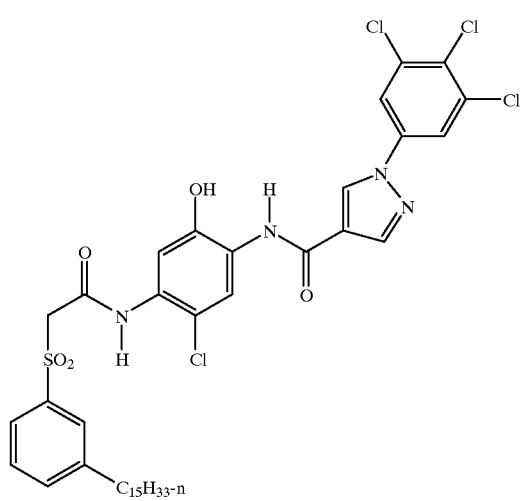
IC-13
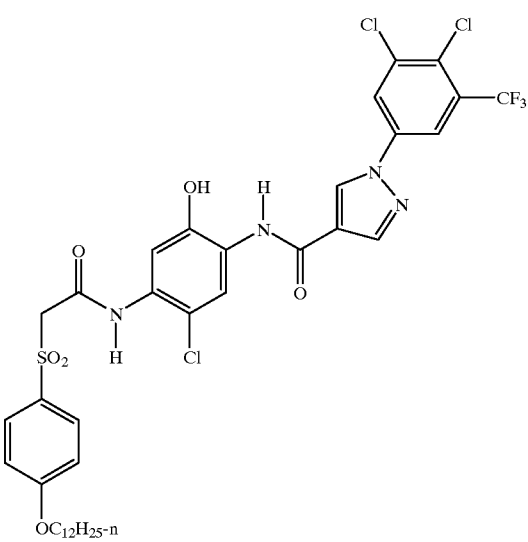
IC-14
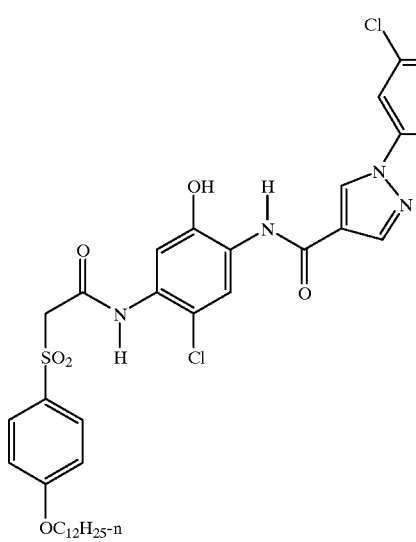
IC-15
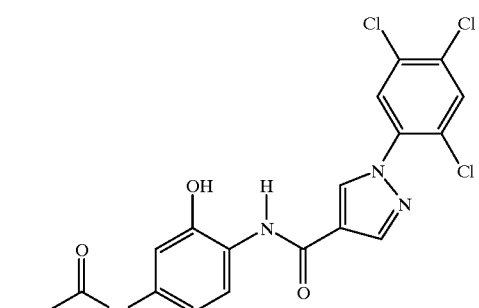
IC-16
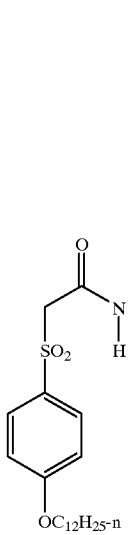
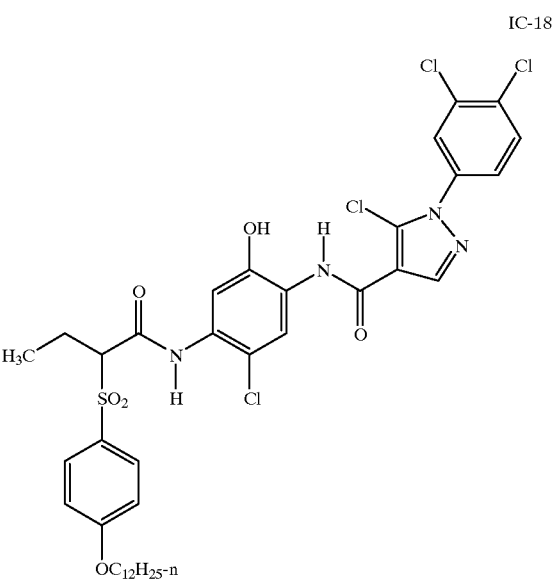
IC-17
IC-18

IC-19
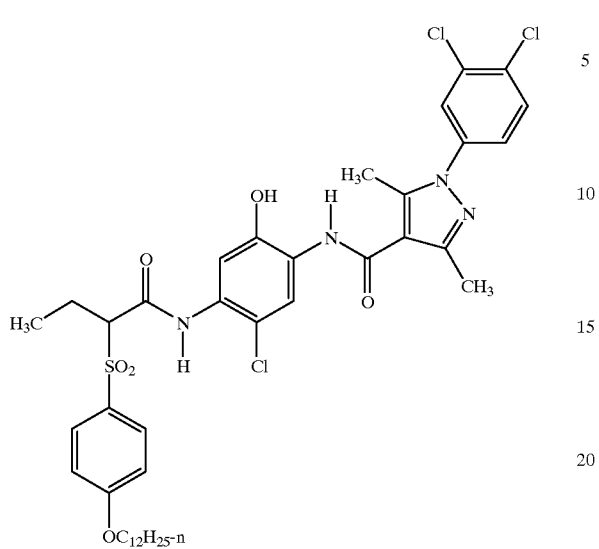
IC-22
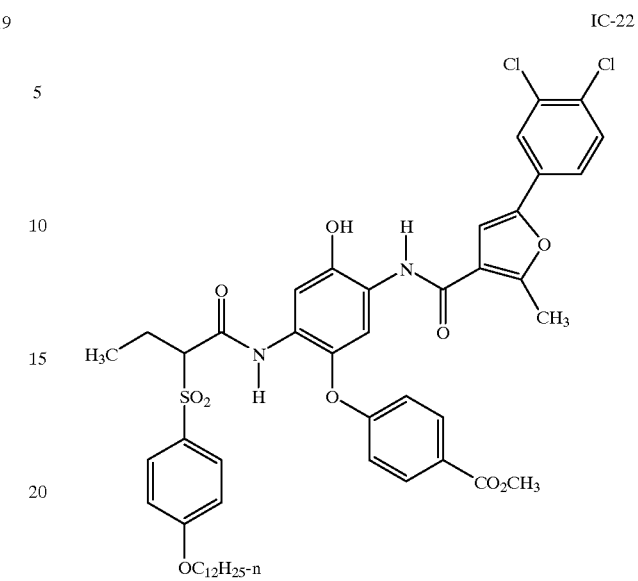
IC-20
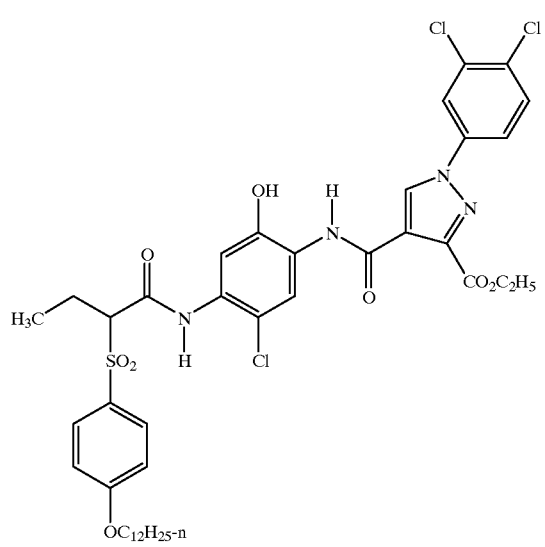
IC-23
IC-21
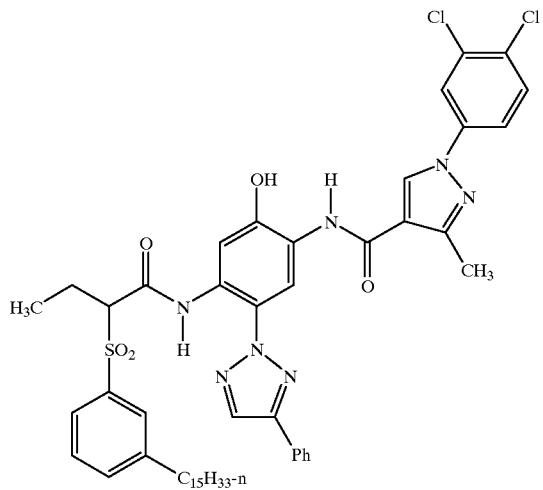
IC-24
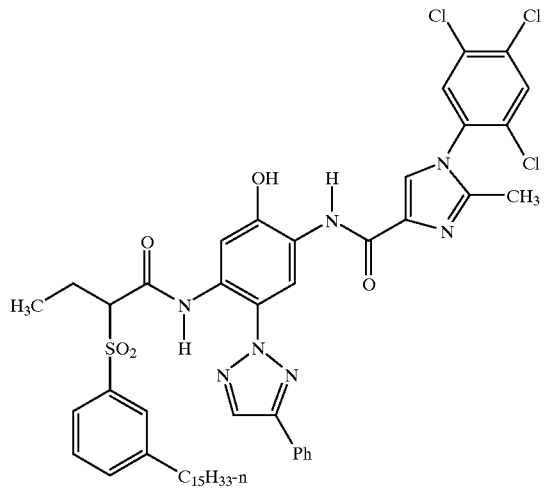

IC-25
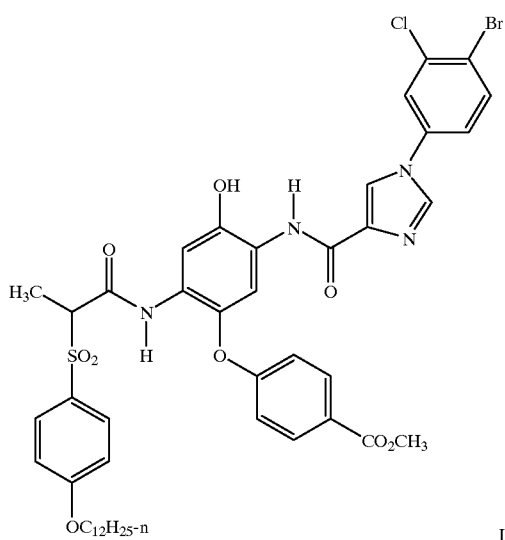
IC-26
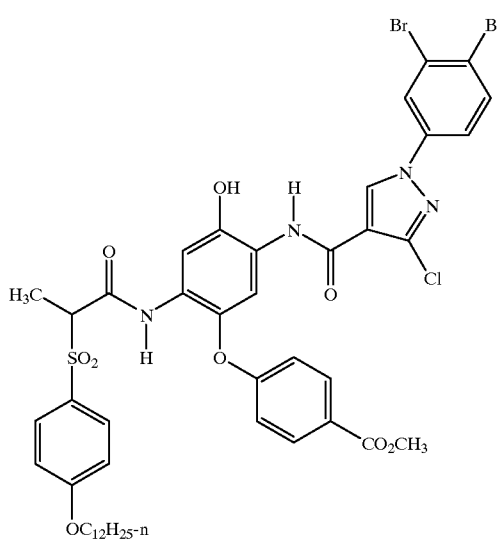
IC-27
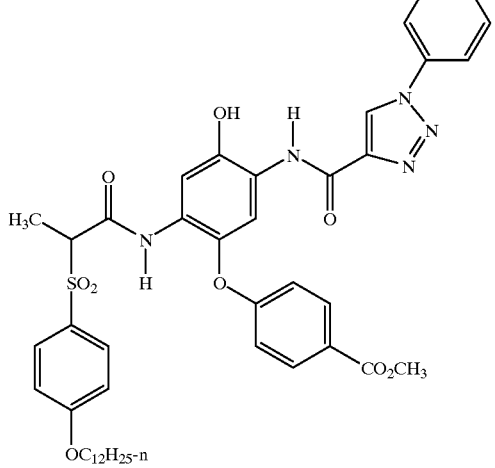
IC-28
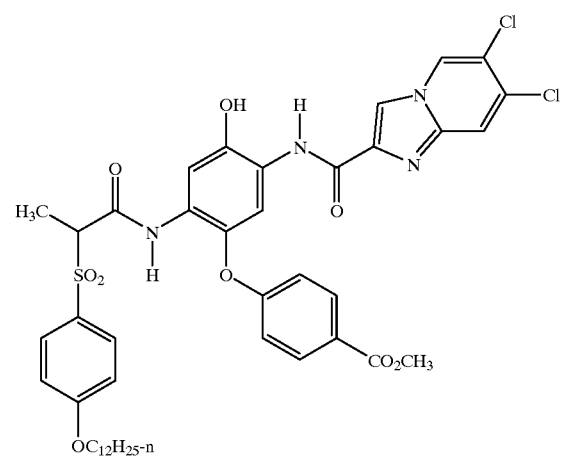
IC-29
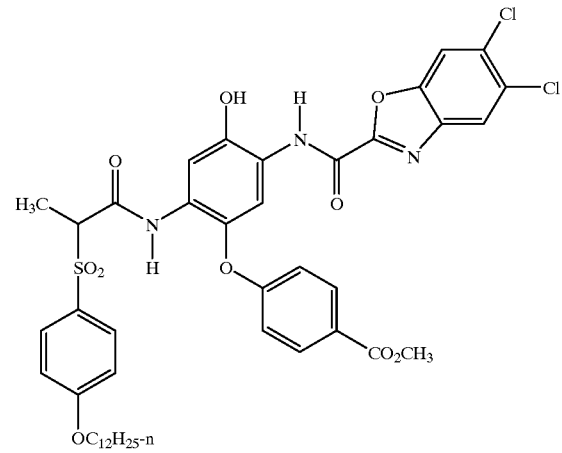
IC-30
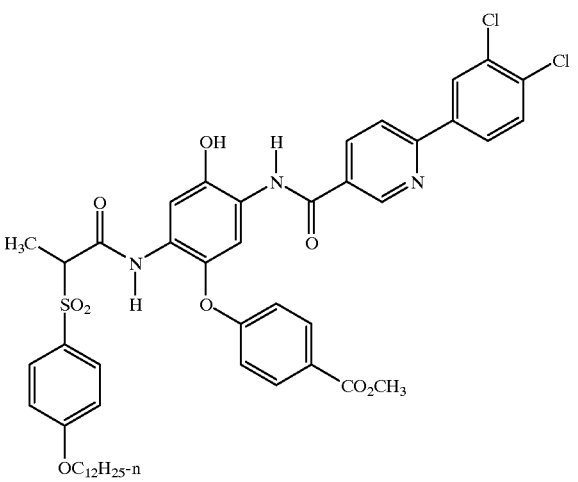
The preferred couplers useful in the invention are capable of forming dyes with color developers such as 4-amino-3-methyl-N-ethyl-N-(2-methanesulfonamidoethyl) aniline sesquisulfate hydrate that have an LBW less than 70 nm. and preferably less than 60 nm. The wavelength of maximum absorption is suitably less than 650 nm. and is typically less than 640 nm.

The coupler of the invention is preferably an "NB coupler" which is a narrow bandwidth coupler of formula (I) having substituents so that there is a reduction in left bandwidth in spin-coating form vs. solution form of at least 5 nm. In accordance with the procedure, a dye is formed by combining the coupler and the developer 4-amino-3-methyl-N-ethyl-N-(2-methanesulfonamidoethyl) aniline sesquisulfate hydrate. If the left bandwidth (LBW) of its absorption spectra upon "spin coating" of a 3% w/v solution of the dye in di-n-butyl sebacate solvent is at least 5 nm. less than the LBW for a solution of the same dye in acetonitrile, then the coupler is an "NB Coupler". The LBW of the spectral curve for a dye is the distance between the left side of the spectral curve and the wavelength of maximum absorption measured at a density of half the maximum.

The "spin coating" sample is prepared by first preparing a solution of the dye in di-n-butyl sebacate solvent (3% w/v). If the dye is insoluble, dissolution is achieved by the addition of methylene chloride. The solution is filtered and 0.1–0.2 ml is applied to a clear polyethylene terephthalate support (approximately 4 cm×4 cm) and spun at 4,000 RPM using the Spin Coating equipment, Model No. EC101, available from Headway Research Inc., Garland Tex. The transmission spectra of the so prepared dye samples are then recorded.

Preferred "NB couplers" form a dye which has a LBW of the absorption spectra upon "spin coating" a sample of the dye in di-n-butyl sebacate which is at least 15 nm, preferably at least 25 nm, less than that of the same dye in acetonitrile solution.

Unless otherwise specifically stated, use of the term "substituted" or "substituent" means any group or atom other than hydrogen. Additionally, when the term "group" is used, it means that when a substituent group contains a substitutable hydrogen, it is also intended to encompass not only the substituent's unsubstituted form, but also its form further substituted with any substituent group or groups as herein mentioned, so long as the substituent does not destroy properties necessary for photographic utility. Suitably, a substituent group may be halogen or may be bonded to the remainder of the molecule by an atom of carbon, silicon, oxygen, nitrogen, phosphorous, or sulfur. The substituent may be, for example, halogen, such as chlorine, bromine or fluorine; nitro; hydroxyl; cyano; carboxyl; or groups which may be further substituted, such as alkyl, including straight or branched chain or cyclic alkyl, such as methyl, trifluoromethyl, ethyl, t-butyl, 3-(2,4-di-t-pentylphenoxy) propyl, and tetradecyl; alkenyl, such as ethylene, 2-butene; alkoxy, such as methoxy, ethoxy, propoxy, butoxy, 2-methoxyethoxy, sec-butoxy, hexyloxy, 2-ethylhexyloxy, tetradecyloxy, 2-(2,4-di-t-pentylphenoxy)ethoxy, and 2-dodecyloxyethoxy; aryl such as phenyl, 4-t-butylphenyl, 2,4,6-trimethylphenyl, naphthyl; aryloxy, such as phenoxy, 2-methylphenoxy, alpha- or beta-naphthyloxy, and 4-tolyloxy; carbonamido, such as acetamido, benzamido, butyramido, tetradecanamido, alpha-(2,4-di-t-pentyl-phenoxy)acetamido, alpha-(2,4-di-t-pentylphenoxy) butyramido, alpha-(3-pentadecylphenoxy)-hexanamido, alpha-(4-hydroxy-3-t-butylphenoxy)-tetradecanamido, 2-oxo-pyrrolidin-1-yl, 2-oxo-5-tetradecylpyrrolin-1-yl, N-methyltetradecanamido, N-succinimido, N-phthalimido, 2,5-dioxo-1-oxazolidinyl, 3-dodecyl-2,5-dioxo-1-imidazolyl, and N-acetyl-N-dodecylamino, ethoxycarbonylamino, phenoxycarbonylamino, benzyloxycarbonylamino, hexadecyloxycarbonylamino, 2,4-di-t-butylphenoxycarbonylamino, phenylcarbonylamino, 2,5-(di-t-pentylphenyl) carbonylamino, p-dodecyl-phenylcarbonylamino, p-tolylcarbonylamino, N-methylureido, N,N-dimethylureido, N-methyl-N-dodecylureido, N-hexadecylureido, N,N-dioctadecylureido, N,N-dioctyl-N'-ethylureido, N-phenylureido, N,N-diphenylureido, N-phenyl-N-p-tolylureido, N-(m-hexadecylphenyl)ureido, N,N-(2,5-di-t-pentylphenyl)-N'-ethylureido, and t-butylcarbonamido; sulfonamido, such as methylsulfonamido, benzenesulfonamido, p-tolylsulfonamido, p-dodecylbenzenesulfonamido, N-methyltetradecylsulfonamido, N,N-dipropylsulfamoylamino, and hexadecylsulfonamido; sulfamoyl, such as N-methylsulfamoyl, N-ethylsulfamoyl, N,N-dipropylsulfamoyl, N-hexadecylsulfamoyl, N,N-dimethylsulfamoyl; N-[3-(dodecyloxy)propyl]sulfamoyl, N-[4-(2,4-di-t-pentylphenoxy)butyl]sulfamoyl, N-methyl-N-tetradecylsulfamoyl, and N-dodecylsulfamoyl; carbamoyl, such as N-methylcarbamoyl, N,N-dibutylcarbamoyl, N-octadecylcarbamoyl, N-[4-(2,4-di-t-pentylphenoxy)butyl]carbamoyl, N-methyl-N-tetradecylcarbamoyl, and N,N-dioctylcarbamoyl; acyl, such as acetyl, (2,4-di-t-amylphenoxy)acetyl, phenoxycarbonyl, p-dodecyloxyphenoxycarbonyl methoxycarbonyl, butoxycarbonyl, tetradecyloxycarbonyl, ethoxycarbonyl, benzyloxycarbonyl, 3-pentadecyloxycarbonyl, and dodecyloxycarbonyl; sulfonyl, such as methoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl, octylsulfonyl, 2-ethylhexylsulfonyl, dodecylsulfonyl, hexadecylsulfonyl, phenylsulfonyl, 4-nonylphenylsulfonyl, and p-tolylsulfonyl; sulfonyloxy, such as dodecylsulfonyloxy, and hexadecylsulfonyloxy; sulfinyl, such as methylsulfinyl, octylsulfinyl, 2-ethylhexylsulfinyl, dodecylsulfinyl, hexadecylsulfinyl, phenylsulfinyl, 4-nonylphenylsulfinyl, and p-tolylsulfinyl; thio, such as ethylthio, octylthio, benzylthio, tetradecylthio, 2-(2,4-di-t-pentylphenoxy)ethylthio, phenylthio, 2-butoxy-5-t-octylphenylthio, and p-tolylthio; acyloxy, such as acetyloxy, benzoyloxy, octadecanoyloxy, p-dodecylamidobenzoyloxy, N-phenylcarbamoyloxy, N-ethylcarbamoyloxy, and cyclohexylcarbonyloxy; amine, such as phenylanilino, 2-chloroanilino, diethylamine, dodecylamine; imino, such as 1-(N-phenylimido)ethyl, N-succinimido or 3-benzylhydantoinyl; phosphate, such as dimethylphosphate and ethylbutylphosphate; phosphite, such as diethyl and dihexylphosphite; a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen and sulfur, such as 2-furyl, 2-thienyl, 2-benzimidazolyloxy or 2-benzothiazolyl; quaternary ammonium, such as triethylammonium; and silyloxy, such as trimethylsilyloxy.

If desired, the substituents may themselves be further substituted one or more times with the described substituent groups. The particular substituents used may be selected by those skilled in the art to attain the desired photographic properties for a specific application and can include, for example, hydrophobic groups, solubilizing groups, blocking groups, and releasing or releasable groups. When a molecule may have two or more substituents, the substituents may be joined together to form a ring such as a fused ring unless otherwise provided. Generally, the above groups and substituents thereof may include those having up to 48 carbon atoms, typically 1 to 36 carbon atoms and usually less than 24 carbon atoms, but greater numbers are possible depending on the particular substituents selected.

The materials of the invention can be used in any of the ways and in any of the combinations known in the art. Typically, the invention materials are incorporated in a melt and coated as a layer described herein on a support to form part of a photographic element. When the term "associated" is employed, it signifies that a reactive compound is in or adjacent to a specified layer where, during processing, it is capable of reacting with other components.

To control the migration of various components, it may be desirable to include a high molecular weight hydrophobe or "ballast" group in coupler molecules. Representative ballast groups include substituted or unsubstituted alkyl or aryl groups containing 8 to 48 carbon atoms. Representative substituents on such groups include alkyl, aryl, alkoxy, aryloxy, alkylthio, hydroxy, halogen, alkoxycarbonyl, aryloxcarbonyl, carboxy, acyl, acyloxy, amino, anilino, carbonamido, carbamoyl, alkylsulfonyl, arylsulfonyl, sulfonamido, and sulfamoyl groups wherein the substituents typically contain 1 to 42 carbon atoms. Such substituents can also be further substituted.

The photographic elements can be single color elements or multicolor elements. Multicolor elements contain image dye-forming units sensitive to each of the three primary regions of the spectrum. Each unit can comprise a single emulsion layer or multiple emulsion layers sensitive to a given region of the spectrum. The layers of the element, including the layers of the image-forming units, can be arranged in various orders as known in the art. In an alternative format, the emulsions sensitive to each of the three primary regions of the spectrum can be disposed as a single segmented layer.

A typical multicolor photographic element comprises a support bearing a cyan dye image-forming unit comprised of at least one red-sensitive silver halide emulsion layer having associated therewith at least one cyan dye-forming coupler, a magenta dye image-forming unit comprising at least one green-sensitive silver halide emulsion layer having associated therewith at least one magenta dye-forming coupler, and a yellow dye image-forming unit comprising at least one blue-sensitive silver halide emulsion layer having associated therewith at least one yellow dye-forming coupler. The element can contain additional layers, such as filter layers, interlayers, overcoat layers, and subbing layers.

If desired, the photographic element can be used in conjunction with an applied magnetic layer as described in *Research Disclosure,* November 1992, Item 34390 published by Kenneth Mason Publications, Ltd., Dudley Annex, 12a North Street, Emsworth, Hampshire P010 7DQ, ENGLAND, and as described in Hatsumi Kyoukai Koukai Gihou No. 94-6023, published Mar. 15, 1994, available from the Japanese Patent Office, the contents of which are incorporated herein by reference. When it is desired to employ the inventive materials in a small format film, *Research Disclosure,* June 1994, Item 36230, provides suitable embodiments.

In the following discussion of suitable materials for use in the emulsions and elements of this invention, reference will be made to *Research Disclosure,* September 1996, Item 38957, available as described above, which is referred to herein by the term "Research Disclosure". The contents of the Research Disclosure, including the patents and publications referenced therein, are incorporated herein by reference, and the Sections hereafter referred to are Sections of the Research Disclosure.

Except as provided, the silver halide emulsion containing elements employed in this invention can be either negative-working or positive-working as indicated by the type of processing instructions (i.e. color negative, reversal, or direct positive processing) provided with the element. Suitable emulsions and their preparation as well as methods of chemical and spectral sensitization are described in Sections I through V. Various additives such as UV dyes, brighteners, antifoggants, stabilizers, light absorbing and scattering materials, and physical property modifying addenda such as hardeners, coating aids, plasticizers, lubricants and matting agents are described, for example, in Sections II and VI through VIII. Color materials are described in Sections X through XIII. Suitable methods for incorporating couplers and dyes, including dispersions in organic solvents, are described in Section X(E). Scan facilitating is described in Section XIV. Supports, exposure, development systems, and processing methods and agents are described in Sections XV to XX. The information contained in the September 1994 *Research Disclosure,* Item No. 36544 referenced above, is updated in the September 1996 *Research Disclosure,* Item No. 38957. Certain desirable photographic elements and processing steps, including those useful in conjunction with color reflective prints, are described in *Research Disclosure,* Item 37038, February 1995.

Coupling-off groups are well known in the art. Such groups can determine the chemical equivalency of a coupler, i.e., whether it is a 2-equivalent or a 4-equivalent coupler, or modify the reactivity of the coupler. Such groups can advantageously affect the layer in which the coupler is coated, or other layers in the photographic recording material, by performing, after release from the coupler, functions such as dye formation, dye hue adjustment, development acceleration or inhibition, bleach acceleration or inhibition, electron transfer facilitation, and color correction.

The presence of hydrogen at the coupling site provides a 4-equivalent coupler, and the presence of another coupling-off group usually provides a 2-equivalent coupler. Representative classes of such coupling-off groups include, for example, chloro, alkoxy, aryloxy, hetero-oxy, sulfonyloxy, acyloxy, acyl, heterocyclyl, sulfonamido, mercaptotetrazole, benzothiazole, mercaptopropionic acid, phosphonyloxy, arylthio, and arylazo. These coupling-off groups are described in the art, for example, in U.S. Pat. Nos. 2,455,169, 3,227,551, 3,432,521, 3,476,563, 3,617,291, 3,880,661, 4,052,212 and 4,134,766; and in UK. Patents and published application Nos. 1,466,728, 1,531,927, 1,533,039, 2,006, 755A and 2,017,704A, the disclosures of which are incorporated herein by reference.

Image dye-forming couplers in addition to those of the invention may be included in the element such as couplers that form cyan dyes upon reaction with oxidized color developing agents which are described in such representative patents and publications as: "Farbkuppler-eine Literature Ubersicht," published in Agfa Mitteilungen, Band III, pp. 156–175 (1961) as well as in U.S. Pat. Nos. 2,367,531; 2,423,730; 2,474,293; 2,772,162; 2,895,826; 3,002,836; 3,034,892; 3,041,236; 4,333,999; 4,746,602; 4,753,871; 4,770,988; 4,775,616; 4,818,667; 4,818,672; 4,822,729; 4,839,267; 4,840,883; 4,849,328; 4,865,961; 4,873,183; 4,883,746; 4,900,656; 4,904,575; 4,916,051; 4,921,783; 4,923,791; 4,950,585; 4,971,898; 4,990,436; 4,996,139; 5,008,180; 5,015,565; 5,011,765; 5,011,766; 5,017,467; 5,045,442; 5,051,347; 5,061,613; 5,071,737; 5,075,207; 5,091,297; 5,094,938; 5,104,783; 5,178,993; 5,813,729; 5,187,057; 5,192,651; 5,200,305 5,202,224; 5,206,130; 5,208,141; 5,210,011; 5,215,871; 5,223,386; 5,227,287; 5,256,526; 5,258,270; 5,272,051; 5,306,610; 5,326,682; 5,366,856; 5,378,596; 5,380,638; 5,382,502; 5,384,236; 5,397,691; 5,415,990; 5,434,034; 5,441,863; EPO 0 246

616; EPO 0 250 201; EPO 0 271 323; EPO 0 295 632; EPO 0 307 927; EPO 0 333 185; EPO 0 378 898; EPO 0 389 817; EPO 0 487 111; EPO 0 488 248; EPO 0 539 034; EPO 0 545 300; EPO 0 556 700; EPO 0 556 777; EPO 0 556 858; EPO 0 569 979; EPO 0 608 133; EPO 0 636 936; EPO 0 651 286; EPO 0 690 344; German OLS 4,026,903; German OLS 3,624,777. and German OLS 3,823,049. Typically such couplers are phenols, naphthols, or pyrazoloazoles.

Couplers that form magenta dyes upon reaction with oxidized color developing agent are described in such representative patents and publications as: "Farbkuppler-eine Literature Ubersicht," published in Agfa Mitteilungen, Band III, pp. 126–156 (1961) as well as U.S. Pat. Nos. 2,311,082 and 2,369,489; 2,343,701; 2,600,788; 2,908,573; 3,062,653; 3,152,896; 3,519,429; 3,758,309; 3,935,015; 4,540,654; 4,745,052; 4,762,775; 4,791,052; 4,812,576; 4,835,094; 4,840,877; 4,845,022; 4,853,319; 4,868,099; 4,865,960; 4,871,652; 4,876,182; 4,892,805; 4,900,657; 4,910,124; 4,914,013; 4,921,968; 4,929,540; 4,933,465; 4,942,116; 4,942,117; 4,942,118; 4,959,480; 4,968,594; 4,988,614; 4,992,361; 5,002,864; 5,021,325; 5,066,575; 5,068,171; 5,071,739; 5,100,772; 5,110,942; 5,116,990; 5,118,812; 5,134,059; 5,155,016; 5,183,728; 5,234,805; 5,235,058; 5,250,400; 5,254,446; 5,262,292; 5,300,407; 5,302,496; 5,336,593; 5,350,667; 5,395,968; 5,354,826; 5,358,829; 5,368,998; 5,378,587; 5,409,808; 5,411,841; 5,418,123; 5,424,179; EPO 0 257 854; EPO 0 284 240; EPO 0 341 204; EPO 347,235; EPO 365,252; E,PO 0 422 595; EPO 0 428 899; EPO 0 428 902; EPO 0 459 331; EPO 0 467 327; EPO 0 476 949; EPO 0 487 081; EPO 0 489 333; EPO 0 512 304; EPO 0 515 128; EPO 0 534 703; EPO 0 554 778; EPO 0 558 145; EPO 0 571 959; EPO 0 583 832; EPO 0 583 834; EPO 0 584 793; EPO 0 602 748; EPO 0 602 749; EPO 0 605 918; EPO 0 622 672; EPO 0 622 673; EPO 0 629 912; EPO 0 646 841, EPO 0 656 561; EPO 0 660 177; EPO 0 686 872; WO 90/10253; WO 92/09010; WO 92/10788; WO 92/12464; WO 93/01523; WO 93/02392; WO 93/02393; WO 93/07534; UK Application 2,244,053; Japanese Application 03192-350; German OLS 3,624,103; German OLS 3,912, 265; and German OLS 40 08 067. Typically such couplers are pyrazolones, pyrazoloazoles, or pyrazolobenzimidazoles that form magenta dyes upon reaction with oxidized color developing agents.

Couplers that form yellow dyes upon reaction with oxidized color developing agent are described in such representative patents and publications as: "Farbkuppler-eine Literature Ubersicht," published in Agfa Mitteilungen; Band III; pp. 112–126 (1961); as well as U.S. Pat. Nos. 2,298,443; 2,407,210; 2,875,057; 3,048,194; 3,265,506; 3,447,928; 4,022,620; 4,443,536; 4,758,501; 4,791,050; 4,824,771; 4,824,773; 4,855,222; 4,978,605; 4,992,360; 4,994,361; 5,021,333; 5,053,325; 5,066,574; 5,066,576; 5,100,773; 5,118,599; 5,143,823; 5,187,055; 5,190,848; 5,213,958; 5,215,877; 5,215,878; 5,217,857; 5,219,716; 5,238,803; 5,283,166; 5,294,531; 5,306,609; 5,328,818; 5,336,591; 5,338,654; 5,358,835; 5,358,838; 5,360,713; 5,362,617; 5,382,506; 5,389,504; 5,399,474; 5,405,737; 5,411,848; 5,427,898; EPO 0 327 976; EPO 0 296 793; EPO 0 365 282; EPO 0 379 309; EPO 0 415 375; EPO 0 437 818; EPO 0 447 969; EPO 0 542 463; EPO 0 568 037; EPO 0 568 196; EPO 0 568 777; EPO 0 570 006; EPO 0 573 761; EPO 0 608 956; EPO 0 608 957; and EPO 0 628 865. Such couplers are typically open chain ketomethylene compounds.

Couplers that form colorless products upon reaction with oxidized color developing agent are described in such representative patents as: UK. 861,138; U.S. Pat. Nos. 3,632, 345; 3,928,041; 3,958,993 and 3,961,959. Typically such couplers are cyclic carbonyl containing compounds that form colorless products on reaction with an oxidized color developing agent.

Couplers that form black dyes upon reaction with oxidized color developing agent are described in such representative patents as U.S. Pat. Nos. 1,939,231; 2,181,944; 2,333,106; and 4,126,461; German OLS No. 2,644,194 and German OLS No. 2,650,764. Typically such couplers are resorcinols or m-aminophenols that form black or neutral products on reaction with oxidized color developing agent.

In addition to the foregoing, so-called "universal" or "washout" couplers may be employed. These couplers do not contribute to image dye-formation. Thus, for example, a naphthol having an unsubstituted carbamoyl or one substituted with a low molecular weight substituent at the 2- or 3-position may be employed. Couplers of this type are described, for example, in U.S. Pat. Nos. 5,026,628, 5,151, 343, and 5,234,800.

It may be useful to use a combination of couplers any of which may contain known ballasts or coupling-off groups such as those described in U.S. Pat. Nos. 4,301,235; 4,853, 319 and 4,351,897. The coupler may contain solubilizing groups such as described in U.S. Pat. No. 4,482,629. The coupler may also be used in association with "wrong" colored couplers (e.g. to adjust levels of interlayer correction) and, in color negative applications, with masking couplers such as those described in EP 213.490; Japanese Published Application 58-172,647; U.S. Pat. Nos. 2,983, 608; 4,070,191; and 4,273,861; German Applications DE 2,706,117 and DE 2,643,965; UK. Patent 1,530,272; and Japanese Application 58-113935. The masking couplers may be shifted or blocked, if desired.

Typically, couplers are incorporated in a silver halide emulsion layer in a mole ratio to silver of 0.05 to 1.0 and generally 0.1 to 0.5. Usually the couplers are dispersed in a high-boiling organic solvent in a weight ratio of solvent to coupler of 0.1 to 10.0 and typically 0.1 to 2.0 although dispersions using no permanent coupler solvent are sometimes employed.

The invention materials may be used in association with materials that release Photographically Useful Groups (PUGS) that accelerate or otherwise modify the processing steps e.g. of bleaching or fixing to improve the quality of the image. Bleach accelerator releasing couplers such as those described in EP 193,389; EP 301,477; U.S. Pat. Nos. 4,163, 669; 4,865,956; and 4,923,784, may be useful. Also contemplated is use of the compositions in association with nucleating agents, development accelerators or their precursors (UK Patent 2,097,140; UK. Patent 2,131,188); electron transfer agents (U.S. Pat. Nos. 4,859,578; 4,912,025); anti-fogging and anti color-mixing agents such as derivatives of hydroquinones, aminophenols, amines, gallic acid; catechol; ascorbic acid; hydrazides; sulfonamidophenols; and non color-forming couplers.

The invention materials may also be used in combination with filter dye layers comprising colloidal silver sol or yellow, cyan, and/or magenta filter dyes, either as oil-in-water dispersions, latex dispersions or as solid particle dispersions. Additionally, they may be used with "smearing" couplers (e.g. as described in U.S. Pat. No. 4,366,237; EP 96,570; U.S. Pat. Nos. 4,420,556; and 4,543,323.) Also, the compositions may be blocked or coated in protected form as described, for example, in Japanese Application 61/258,249 or U.S. Pat. No. 5,019,492.

The invention materials may further be used in combination with image-modifying compounds that release PUGS such as "Developer Inhibitor-Releasing" compounds (DIR's). DIR's useful in conjunction with the compositions of the invention are known in the art and examples are described in U.S. Pat. Nos. 3,137,578; 3,148,022; 3,148,062; 3,227,554; 3,384,657; 3,379,529; 3,615,506; 3,617,291; 3,620,746; 3,701,783; 3,733,201; 4,049,455; 4,095,984; 4,126,459; 4,149,886; 4,150,228; 4,211,562; 4,248,962; 4,259,437; 4,362,878; 4,409,323; 4,477,563; 4,782,012; 4,962,018; 4,500,634; 4,579,816; 4,607,004; 4,618,571; 4,678,739; 4,746,600; 4,746,601; 4,791,049; 4,857,447; 4,865,959; 4,880,342; 4,886,736; 4,937,179; 4,946,767; 4,948,716; 4,952,485; 4,956,269; 4,959,299; 4,966,835; 4,985,336 as well as in patent publications GB 1,560,240; GB 2,007,662; GB 2,032,914; GB 2,099,167; DE 2,842,063, DE 2,937,127; DE 3,636,824; DE 3,644,416 as well as the following European Patent Publications: 272,573; 335,319; 336,411; 346, 899; 362, 870; 365,252; 365,346; 373,382; 376,212; 377,463; 378,236; 384,670; 396,486; 401,612; 401,613.

Such compounds are also disclosed in "Developer-Inhibitor-Releasing (DIR) Couplers for Color Photography," C. R. Barr, J. R. Thirtle and P. W. Vittum in *Photographic Science and Engineering*, Vol. 13, p. 174 (1969), incorporated herein by reference. Generally, the developer inhibitor-releasing (DIR) couplers include a coupler moiety and an inhibitor coupling-off moiety (IN). The inhibitor-releasing couplers may be of the time-delayed type (DIAR couplers) which also include a timing, moiety or chemical switch which produces a delayed release of inhibitor. Examples of typical inhibitor moieties are: oxazoles, thiazoles, diazoles, triazoles, oxadiazoles, thiadiazoles, oxathiazoles, thiatriazoles, benzotriazoles, tetrazoles, benzimidazoles, indazoles, isoindazoles, mercaptotetrazoles, selenotetrazoles, mercaptobenzothiazoles, selenobenzothiazoles, mercaptobenzoxazoles, selenobenzoxazoles, mercaptobenzimidazoles, selenobenzimidazoles, benzodiazoles, mercaptooxazoles, mercaptothiadiazoles, mercaptothiazoles, mercaptotriazoles, mercaptooxadiazoles, mercaptodiazoles, mercaptooxathiazoles, telleurotetrazoles or benzisodiazoles. In a preferred embodiment, the inhibitor moiety or group is selected from the following formulas:

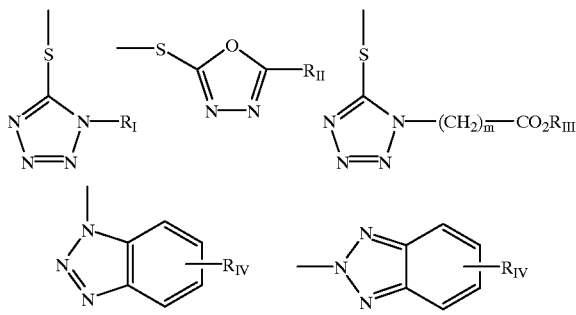

wherein $R_I$ is selected from the group consisting of straight and branched alkyls of from 1 to about 8 carbon atoms, benzyl, phenyl, and alkoxy groups and such groups containing none, one or more than one such substituent; $R_{II}$ is selected from $R_I$ and —$SR_I$; $R_{III}$ is a straight or branched alkyl group of from 1 to about 5 carbon atoms and m is from 1 to 3; and $R_{IV}$ is selected from the group consisting of hydrogen, halogens and alkoxy, phenyl and carbonamido groups, —$COOR_V$ and —$NHCOOR_V$ wherein $R_V$ is selected from substituted and unsubstituted alkyl and aryl groups.

Although it is typical that the coupler moiety included in the developer inhibitor-releasing coupler forms an image dye corresponding to the layer in which it is located, it may also form a different color as one associated with a different film layer. It may also be useful that the coupler moiety included in the developer inhibitor-releasing coupler forms colorless products and/or products that wash out of the photographic material during processing (so-called "universal" couplers).

A compound such as a coupler may release a PUG directly upon reaction of the compound during processing, or indirectly through a timing or linking group. A timing group produces the time-delayed release of the PUG such groups using an intramolecular nucleophilic substitution reaction (U.S. Pat. No. 4,248,962); groups utilizing an electron transfer reaction along a conjugated system (U.S. Pat. Nos. 4,409,323; 4,421,845; 4,861,701, Japanese Applications 57-188035; 58-98728; 58-209736; 58-209738); groups that function as a coupler or reducing agent after the coupler reaction (U.S. Pat. Nos. 4,438,193; 4,618,571) and groups that combine the features describe above. It is typical that the timing group is of one of the formulas:

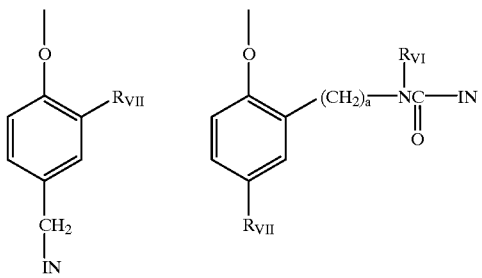

wherein IN is the inhibitor moiety, $R_{VII}$ is selected from the group consisting of nitro, cyano, alkylsulfonyl; sulfamoyl; and sulfonamido groups; a is 0 or 1; and $R_{VI}$ is selected from the group consisting of substituted and unsubstituted alkyl and phenyl groups. The oxygen atom of each timing group is bonded to the coupling-off position of the respective coupler moiety of the DIAR.

The timing or linking groups may also function by electron transfer down an unconjugated chain. Linking groups are known in the art under various names. Often they have been referred to as groups capable of utilizing a hemiacetal or iminoketal cleavage reaction or as groups capable of utilizing a cleavage reaction due to ester hydrolysis such as U.S. Pat. No. 4,546,073. This electron transfer down an unconjugated chain typically results in a relatively fast decomposition and the production of carbon dioxide, formaldehyde, or other low molecular weight by-products. The groups are exemplified in EP 464,612, EP 523,451, U.S. Pat. No. 4,146,396, Japanese Kokai 60-249148 and 60-249149.

Suitable developer inhibitor-releasing couplers for use in the present invention include, but are not limited to, the following:

D1 D2 D3 D4 D5 D6 D7 D8 D9

D10

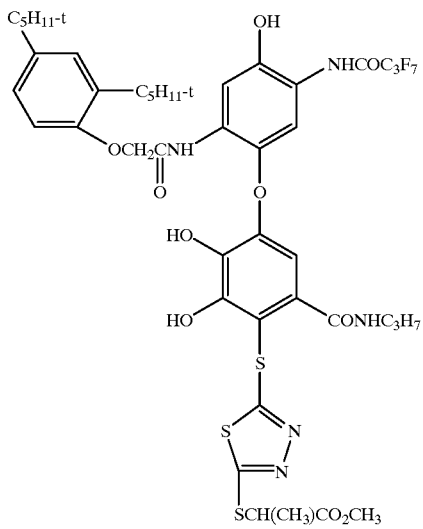

D11

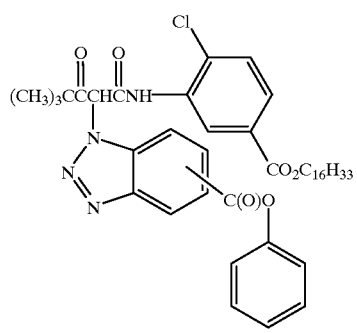

D12

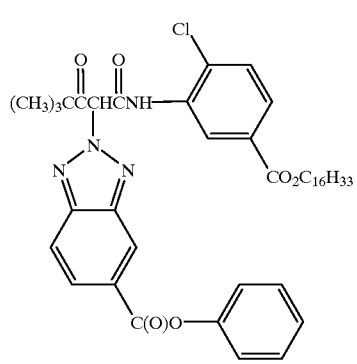

It is also contemplated that the concepts of the present invention may be employed to obtain reflection color prints as described in Research Disclosure, November 1979, Item 18716, available from Kenneth Mason Publications, Ltd, Dudley Annex, 12a North Street, Emsworth, Hampshire P0101 7DQ, England, incorporated herein by reference. Materials of the invention may be coated on pH adjusted support as described in U.S. Pat. No. 4,917,994; on a support with reduced oxygen permeability (EP 553,339); with epoxy solvents (EP 164,961); with nickel complex stabilizers (U.S. Pat. Nos. 4,346,165; 4,540,653 and 4,906,559 for example); with ballasted chelating agents such as those in U.S. Pat. No. 4,994,359 to reduce sensitivity to polyvalent cations such as calcium; and with stain reducing compounds such as described in U.S. Pat. No. 5,068,171. Other compounds useful in combination with the invention are disclosed in Japanese Published Applications described in Derwent Abstracts having accession numbers as follows: 90-072,629, 90-072,630; 90-072,631; 90-072,632; 90-072,633; 90-072,634; 90-077,822; 90-078,229; 90-078,230; 90-079,336; 90-079,337; 90-079,338; 90-079,690; 90-079,691; 90-080,487; 90-080,488; 90-080,489; 90-080,490; 90-080,491; 90-080,492; 90-080,494; 90-085,928; 90-086,669; 90-086,670; 90-087,360; 90-087,361; 90-087,362; 90-087,363; 90-087,364; 90-088,097; 90-093,662; 90-093,663; 90-093,664; 90-093,665; 90-093,666; 90-093,668; 90-094,055; 90-094,056; 90-103,409; 83-62,586; 83-09,959.

Conventional radiation-sensitive silver halide emulsions can be employed in the practice of this invention. Such emulsions are illustrated by Research Disclosure, Item 38755, September 1996, I. Emulsion grains and their preparation.

Especially useful in this invention are tabular grain silver halide emulsions. Tabular grains are those having two parallel major crystal faces and having an aspect ratio of at least 2. The term "aspect ratio" is the ratio of the equivalent circular diameter (ECD) of a grain major face divided by its thickness (t). Tabular grain emulsions are those in which the tabular grains account for at least 50 percent (preferably at least 70 percent and optimally at least 90 percent) of the total grain projected area. Preferred tabular grain emulsions are those in which the average thickness of the tabular grains is less than 0.3 micrometer (preferably thin—that is, less than 0.2 micrometer and most preferably ultrathin—that is, less than 0.07 micrometer). The major faces of the tabular grains can lie in either {111} or {100} crystal planes. The mean ECD of tabular grain emulsions rarely exceeds 10 micrometers and more typically is less than 5 micrometers.

In their most widely used form tabular grain emulsions are high bromide {111} tabular grain emulsions. Such emulsions are illustrated by Kofron et al U.S. Pat. No. 4,439,520, Wilgus et al U.S. Pat. No. 4,434,226, Solberg et al U.S. Pat. No. 4,433,048, Maskasky U.S. Pat. Nos. 4,435,501, 4,463,087 and 4,173,320, Daubendiek et al U.S. Pat. Nos. 4,414,310 and 4,914,014, Sowinski et al U.S. Pat. No. 4,656,122, Piggin et al U.S. Pat. Nos. 5,061,616 and 5,061,609, Tsaur et al U.S. Pat. Nos. 5,147,771, '772, '773, 5,171,659 and 5,252,453, Black et al U.S. Pat. Nos. 5,219,720 and 5,334,495, Delton U.S. Pat. Nos. 5,310,644, 5,372,927 and 5,460,934, Wen U.S. Pat. No. 5,470,698, Fenton et al U.S. Pat. No. 5,476,760, Eshelman et al U.S. Pat. Nos. 5,612,175 and 5,614,359, and Irving et al U.S. Pat. No. 5,667,954.

Ultrathin high bromide {111} tabular grain emulsions are illustrated by Daubendiek et al U.S. Pat. Nos. 4,672,027, 4,693,964, 5,494,789, 5,503,971 and 5,576,168, Antoniades et al U.S. Pat. No. 5,250,403, Olm et al U.S. Pat. No. 5,503,970, Deaton et al U.S. Pat. No. 5,582,965, and Maskasky U.S. Pat. No. 5,667,955.

High bromide {100} tabular grain emulsions are illustrated by Mignot U.S. Pat. Nos. 4,386,156 and 5,386,156.

High chloride {111} tabular grain emulsions are illustrated by Wey U.S. Pat. No. 4,399,215, Wey et al U.S. Pat. No. 4,414,306, Maskasky U.S. Pat. Nos. 4,400,463, 4,713,323, 5,061,617, 5,178,997, 5,183,732, 5,185,239, 5,399,478 and 5,411,852, and Maskasky et al U.S. Pat. Nos. 5,176,992 and 5,178,998. Ultrathin high chloride {111} tabular grain emulsions are illustrated by Maskasky U.S. Pat. Nos. 5,271,858 and 5,389,509.

High chloride {100} tabular grain emulsions are illustrated by Maskasky U.S. Pat. Nos. 5,264,337, 5,292,632, 5,275,930 and 5,399,477, House et al U.S. Pat. No. 5,320,938, Brust et al U.S. Pat. No. 5,314,798, Szajewski et al U.S.

Pat. No. 5,356,764, Chang et al U.S. Pat. Nos. 5,413,904 and 5,663,041, Oyamada U.S. Pat. No. 5,593,821, Yamashita et al U.S. Pat. Nos. 5,641,620 and 5,652,088, Saitou et al U.S. Pat. No. 5,652,089, and Oyamada et al U.S. Pat. No. 5,665,530. Ultrathin high chloride {100} tabular grain emulsions can be prepared by nucleation in the presence of iodide, following the teaching of House et al and Chang et al, cited above.

The emulsions can be surface-sensitive emulsions, i.e., emulsions that form latent images primarily on the surfaces of the silver halide grains, or the emulsions can form internal latent images predominantly in the interior of the silver halide grains. The emulsions can be negative-working emulsions, such as surface-sensitive emulsions or unfogged internal latent image-forming emulsions, or direct-positive emulsions of the unfogged, internal latent image-forming type, which are positive-working when development is conducted with uniform light exposure or in the presence of a nucleating agent. Tabular grain emulsions of the latter type are illustrated by Evans et al. U.S. Pat. No. 4,504,570.

Photographic elements can be exposed to actinic radiation, typically in the visible region of the spectrum, to form a latent image and can then be processed to form a visible dye image. Processing to form a visible dye image includes the step of contacting the element with a color developing agent to reduce developable silver halide and oxidize the color developing agent. Oxidized color developing agent in turn reacts with the coupler to yield a dye. If desired "Redox Amplification" as described in Research Disclosure XVIIIB(5) may be used.

With negative-working silver halide, the processing step described above provides a negative image. One type of such element, referred to as a color negative film, is designed for image capture. Speed (the sensitivity of the element to low light conditions) is usually critical to obtaining sufficient image in such elements. Such elements are typically silver bromoiodide emulsions coated on a transparent support and are sold packaged with instructions to process in known color negative processes such as the Kodak C-41 process as described in The British Journal of Photography Annual of 1988, pages 191–198. If a color negative film element is to be subsequently employed to generate a viewable projection print as for a motion picture, a process such as the Kodak ECN-2 process described in the H-24 Manual available from Eastman Kodak Co. may be employed to provide the color negative image on a transparent support. Color negative development times are typically 3' 15" or less and desirably 90 or even 60 seconds or less.

The photographic element of the invention can be incorporated into exposure structures intended for repeated use or exposure structures intended for limited use, variously referred to by names such as "single use cameras", "lens with film", or "photosensitive material package units".

Another type of color negative element is a color print. Such an element is designed to receive an image optically printed from an image capture color negative element. A color print element may be provided on a reflective support for reflective viewing (e.g. a snap shot) or on a transparent support for projection viewing as in a motion picture. Elements destined for color reflection prints are provided on a reflective support, typically paper, employ silver chloride emulsions, and may be optically printed using the so-called negative-positive process where the element is exposed to light through a color negative film which has been processed as described above. The element is sold packaged with instructions to process using a color negative optical printing process, for example the Kodak RA-4 process, as generally described in PCT WO 87/04534 or U.S. Pat. No. 4,975,357, to form a positive image. Color projection prints may be processed, for example, in accordance with the Kodak ECP-2 process as described in the H-24 Manual. Color print development times are typically 90 seconds or less and desirably 45 or even 30 seconds or less.

A reversal element is capable of forming a positive image without optical printing. To provide a positive (or reversal) image, the color development step is preceded by development with a non-chromogenic developing agent to develop exposed silver halide, but not form dye, and followed by uniformly fogging the element to render unexposed silver halide developable. Such reversal elements are typically sold packaged with instructions to process using a color reversal process such as the Kodak E-6 process as described in The British Journal of Photography Annual of 1988, page 194. Alternatively, a direct positive emulsion can be employed to obtain a positive image.

The above elements are typically sold with instructions to process using the appropriate method such as the mentioned color negative (Kodak C-41), color print (Kodak RA-4), or reversal (Kodak E-6) process.

Preferred color developing agents are p-phenylenediamines such as:

4-amino-N,N-diethylaniline hydrochloride,
4-amino-3-methyl-N,N-diethylaniline hydrochloride,
4-amino-3-methyl-N-ethyl-N-(2-methanesulfonamidoethyl) aniline sesquisulfate hydrate,
4-amino-3-methyl-N-ethyl-N-(2-hydroxyethyl)aniline sulfate,
4-amino-3-(2-methanesulfonamidoethyl)-N,N-diethylaniline hydrochloride, and
4-amino-N-ethyl-N-(2-methoxyethyl)-m-toluidine di-p-toluene sulfonic acid.

Development is usually followed by the conventional steps of bleaching, fixing, or bleach-fixing, to remove silver or silver halide, washing, and drying The compound of the invention is a coupler compound as described in the foregoing description of the photographic element. The process of the invention includes a method of forming an image in the described silver halide element after the same has been exposed to light comprising contacting the exposed element with a color developing compound such as a para phenylene diamine.

A direct-view photographic element is defined as one which yields a color image that is designed to be viewed directly (1) by reflected light, such as a photographic paper print, (2) by transmitted light, such as a display transparency, or (3) by projection, such as a color slide or a motion picture print. These direct-view elements may be exposed and processed in a variety of ways. For example, paper prints, display transparencies, and motion picture prints are typically produced by optically printing an image from a color negative onto the direct-viewing element and processing though an appropriate negative-working photographic process to give a positive color image. Color slides may be produced in a similar manner but are more typically produced by exposing the film directly in a camera and processing through a reversal color process or a direct positive process to give a positive color image. The image may also be produced by alternative processes such as digital printing.

Each of these types of photographic elements has its own particular requirements for dye hue, but in general they all require cyan dyes that whose absorption bands are less deeply absorbing (that is, shifted away from the red end of the spectrum) than color negative films. This is because dyes in direct viewing elements are selected to have the best appearance when viewed by human eyes, whereas the dyes in color negative materials designed for optical printing are designed to best match the spectral sensitivities of the print materials.

The compound of the invention is the coupler compound as described in the foregoing description of the photographic element. The process of the invention includes a method of forming an image in the described silver halide element after the same has been exposed to light comprising contacting the exposed element with a color developing compound such as a para phenylene diamine.

SYNTHESIS EXAMPLE

The following is an example of how the couplers of the current invention may be synthesized.

5-Chloro-2-methyl-6-nitrobenzoxazole (2)

Concentrated sulfuric acid (150 mL) was stirred mechanically and cooled in an ice/water bath. To this was gradually added 5-chloro-2-methylbenzoxazole (1), (75 g, 0.45 Moles) at such a rate that the temperature stayed at 30° C., over a 15–20 minute period. A solution of concentrated sulfuric acid (40 mL), and concentrated nitric acid (32 mL), was prepared and added drop by drop to the benzoxazole solution at such a rate that the temperature was maintained at approximately 20° C. When this acid solution had been added the cooling bath was removed and the mixture allowed to stir at room temperature for 1 hour. At the end of this period the solution was carefully poured onto ice with good stirring. Sufficient water was then added to get good mixing. The solid was filtered off, washed well with water followed by methanol and finally air dried. Yield 90.6 g.

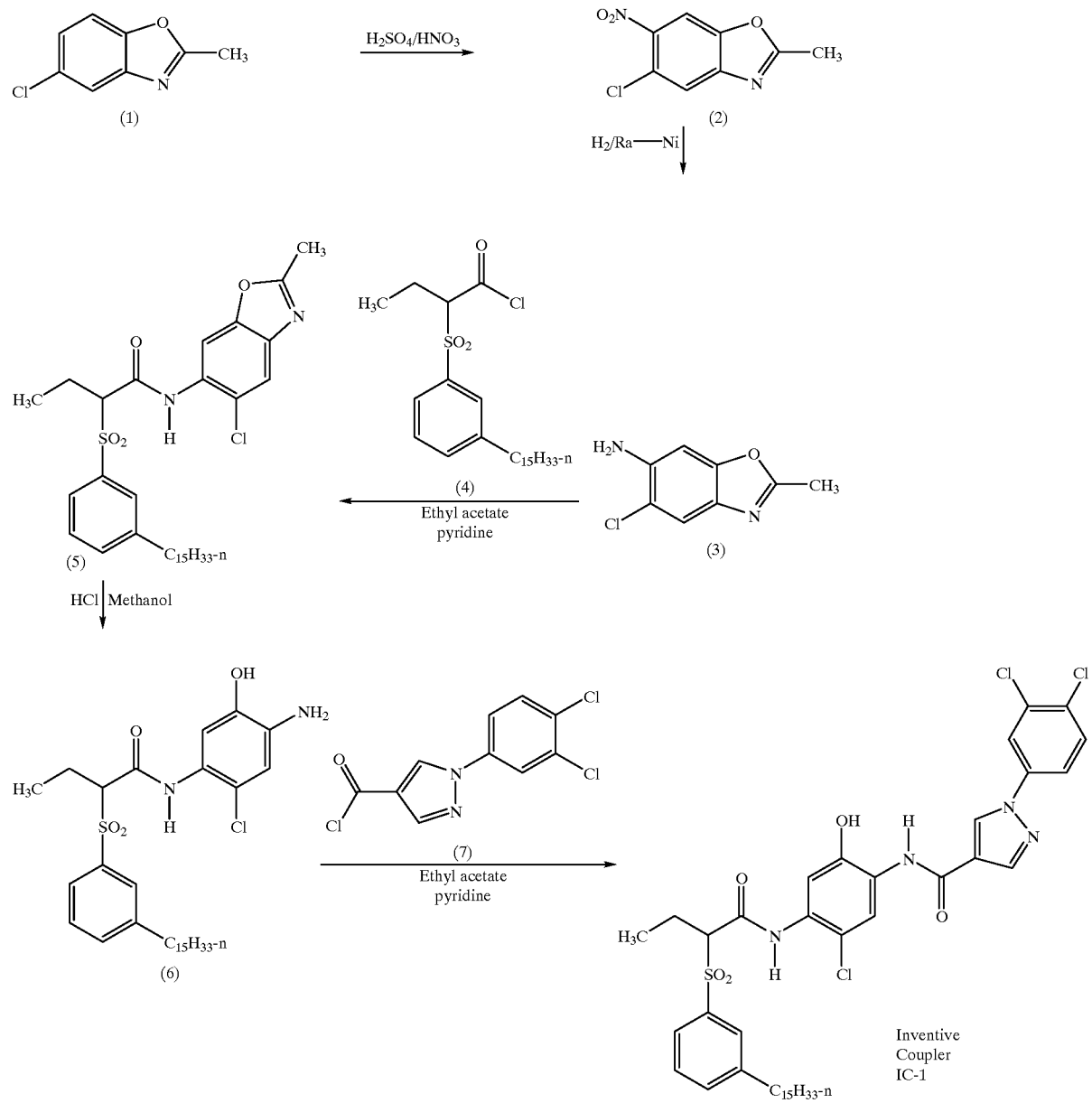

6-Amino-5-Chloro-2-methylbenzoxazole (3)

Compound (2), (30 g), was dissolved in tetrahydrofuran (150 mL), and Raney-Nickel which had been pre-washed with water (×3) and tetrahydrofuran (×3), was added. The mixture was then hydrogenated at room temperature and 50 psi of hydrogen. The reaction is complete in approximately 1.5 hours. After this period, the catalyst is filtered off and the solution concentrated under reduced pressure. The residue is triturated with heptane, cooled and the solid filtered off. Yield 22 g.

2-[(3-Pentadecylphenyl)sulfonyl]butanoyl chloride, (4)

2-[(3-Pentadecylphenyl)sulfonyl]butanoic acid (84.6 g, 0.193 Mole) was suspended in ethyl acetate (700 mL) to which was added dimethylformamide (0.5 mL) and thionyl chloride (70 mL, 0.964 Mole). The mixture was heated at 70° C. for 1.5 hours, cooled, concentrated under reduced pressure, co-evaporated with ethyl acetate (2×100 mL) and the oil so obtained used as such in the next step of the reaction sequence.

Compound (5)

6-Amino-5-Chloro-2-methylbenzoxazole (3), (32.0 g, 0.175 Mole) was dissolved in ethyl acetate (500 mL) with dry pyridine (15.6 mL, 0.193 Mole). The 2-[(3-pentadecylphenyl)sulfonyl]butanoyl chloride, (4), (0.193 Mole) dissolved in ethyl acetate (200 mL) was then added to the solution at a fairly fast drip rate over a 15 minute period while maintaining good stirring and keeping the temperature below 30° C. At the end of the addition, the cooling bath was removed and the reaction mixture stirred at room temperature for an additional 15 minutes. The reaction mixture was then washed with 2N-HCl (3×200 mL), dried (MgSO$_4$), filtered and concentrated to an oil. This oil was then taken on to the next step.

Compound (6)

Compound (5), (0.175 Mole) was dissolved in methanol (800 mL) and concentrated hydrochloric acid (40 mL) added. The mixture was heated to 70° C. and after about 10 minutes complete dissolution of the initially precipitated material was achieved. After 1 hour a further volume of concentrated hydrochloric acid (20 mL) was added followed by 2 additional volumes (20 mL each) at 30 minute intervals. After the last volume had been added, the solution was heated for 30 more minutes, cooled and concentrated under reduced pressure until the product began to crystallize. Diethyl ether (1.0 L) was added and the mixture cooled overnight to 0° C. Following morning the product was filtered off, washed with diethyl ether and air dried. Yield 100 g.

Inventive Coupler (IC-1)

Compound (6) (7.4 g, 13.08 mMole), was suspended in ethyl acetate (70 mL), heated to 60° C. with good stirring and dry pyridine (2.1 mL, 26.44 mL) added. After 10 minutes 1-(3,4-dichlorophenyl)-1H-pyrazole-4-carbonyl chloride (7), (13.22 mMole) in ethyl acetate (20 mL) added drop by drop over a 15–20 minute period. Stirring at 60° C. was continued for a further 15–30 minutes after the addition. The reaction mixture was then cooled, diluted with ethyl acetate washed with 2N-HCl(2×50 mL), dried (MgSO$_4$), filtered and concentrated under reduced pressure. The residue was dissolved in 30%-ethyl acetate in heptane, filtered and set aside to crystallize. The inventive coupler IC-1, was filtered off, washed with a little 30%-ethyl acetate in heptane and air-dried. Yield 7. g.

PHOTOGRAPHIC EXAMPLES

Preparation of Photographic Elements

On a gel-subbed, polyethylene-coated paper support were coated the following layers:

First Layer

An underlayer containing 3.23 grams gelatin per square meter.

Second Layer

A photosensitive layer containing (per square meter) 2.15 grams gelatin, an amount of red-sensitized silver chloride emulsion containing the amount of silver (determined by the equivalency of the coupler) indicated in the tables; a dispersion containing $8.61 \times 10^{-4}$ mole of the coupler indicated in Table 2, 3, or 4; and 0.043 gram surfactant Alkanol XC (trademark of E. I. Dupont Co.)(in addition to the Alkanol XC used to prepare the coupler dispersion). The coupler dispersion contained the coupler, all of the gelatin in the layer except that supplied by the emulsion, an amount of the coupler solvent indicated in Table 2, 3, or 4 equal to the weight of coupler, and 0.22 gram Alkanol XC. The uv absorber UV-1, was added in an amount equal to 1.5 molar equivalents of the inventive coupler.

Third Layer

A protective layer containing (per square meter) 1.40 grams gelatin, 0.15 gram bis(vinylsulfonyl)methane, 0.043 gram Alkanol XC, and $4.40 \times 10^{-6}$ gram tetraethylammonium perfluorooctanesulfonate.

The coupler solvent and UV absorber used were:

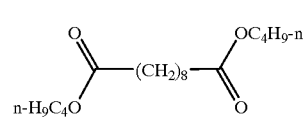

S-1

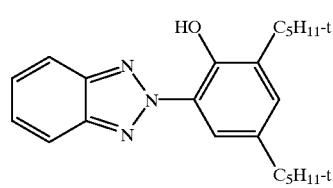

UV-1

Preparation of Processed Photographic Examples

Processed samples were prepared by exposing the coatings through a step wedge and processing as follows:

| Process Step | Time (min.) | Temp. (° C.) |
| --- | --- | --- |
| Developer | 0.75 | 35.0 |
| Bleach-Fix | 0.75 | 35.0 |
| Water wash | 1.50 | 35.0 |

The processing solutions used in the above process had the following compositions (amounts per liter of solution):

| Developer | |
| --- | --- |
| Triethanolamine | 12.41 g |
| Blankophor REU (trademark of Mobay Corp.) | 2.30 g |
| Lithium polystyrene sulfonate | 0.09 g |
| N,N-Diethylhydroxylamine | 4.59 g |

| -continued | |
|---|---|
| Lithium sulfate | 2.70 g |
| Developing agent Dev-1 | 5.00 g |
| 1-Hydroxyethyl-1,1-diphosphonic acid | 0.49 g |
| Potassium carbonate, anhydrous | 21.16 g |
| Potassium chloride | 1.60 g |
| Potassium bromide | 7.00 mg |
| pH adjusted to 10.4 at 26.7° C. | |
| Bleach-Fix | |
| Solution of ammonium thiosulfate | 71.85 g |
| Ammonium sulfite | 5.10 g |
| Sodium metabisulfite | 10.00 g |
| Acetic acid | 10.20 g |
| Ammonium ferric ethylenediaminetetraacetate | 48.58 g |
| Ethylenediaminetetraacetic acid | 3.86 g |
| pH adjusted to 6.7 at 26.7° C. | |

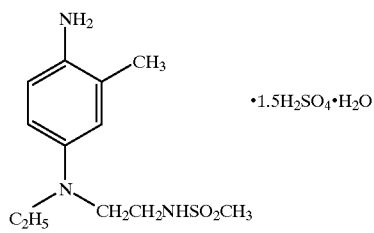

Dev-1

The spectra of the resulting dyes were measured and normalized to a maximum absorption of 1.00. The wavelength of maximum absorption was recorded as the "$\lambda_{max}$." As a measure of the sharpness of the curve on the left (short wavelength) side of the absorption band the "left bandwidth" (LBW) was obtained by subtracting the wavelength at the point on the left side of the absorption band where the normalized density is 0.50 from the $\lambda_{max}$. A lower value of LBW indicates a reduction in the unwanted green absorption and is thus desirable. The $\lambda_{max}$ and LBW values are shown in Table 1.

TABLE I

Photographic Data

| Comparison or Invention | Coupler | Solvent | $\lambda_{max}$ nm | LBW nm |
|---|---|---|---|---|
| Comparison | Comp-1 | S-1 | 627 | 46 |
| Comparison | Comp-2 | S-1 | 633 | 48 |
| Comparison | Comp-3 | S-1 | 661 | 81 |
| Comparison | Comp-4 | S-1 | 651 | 84 |
| Invention | IC-1 | S-1 | 623 | 38 |
| Invention | IC-2 | S-1 | 622 | 37 |

It can be seen from Table I that the couplers of the invention give superior dyes to the dyes of the comparison couplers. The couplers of the invention are hypsochromic (shifted towards the blue region of the spectrum) to the dyes of the comparison couplers and also, have narrower bandwidths.

Procedure for Determining Fade

The photographic elements were protected with a clear support containing 860 mg/m² of UV-absorber, UV-1, and then subjected to a 50Klux light source, balanced for daylight, for a period of 4 weeks. The elements were then read in a Status A densitometer at density level 1.0. The loss in dye density is the difference between the initial reading before exposure to the light and the reading after a 4 week exposure, and is expressed in Table II as, Fade: % Change in Dye Density After 4 Weeks. It can be seen from Table II that the couplers of the invention are superior in light stability to the comparison couplers.

TABLE II

Light Stability Data

| Comparison or Invention | Coupler | Fade: % Change in Dye Density After 4 Weeks |
|---|---|---|
| Comparison | Comp-1 | −22 |
| Comparison | Comp-2 | −23 |
| Comparison | Comp-3 | −20 |
| Comparison | Comp-4 | −47 |
| Invention | IC-1 | −2 |
| Invention | IC-2 | −2 |

The comparison couplers used were;

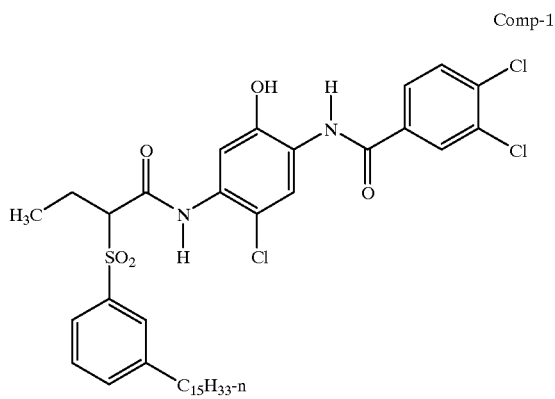

Comp-1

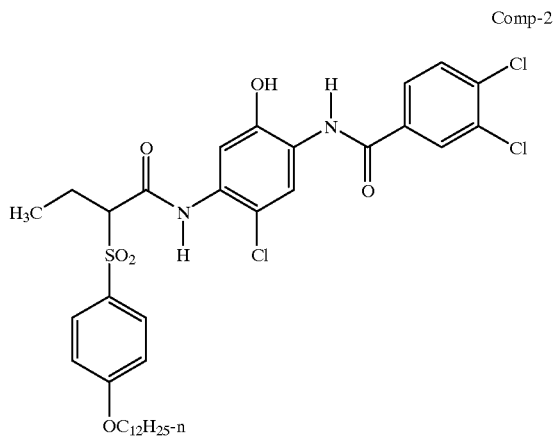

Comp-2

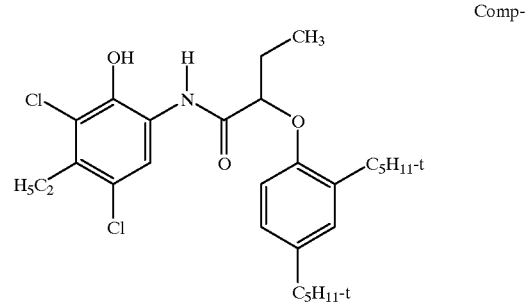

Comp-3

-continued

Comp-4

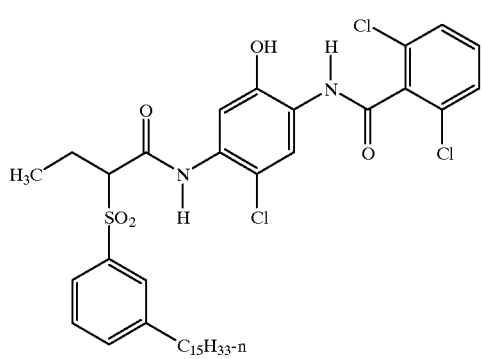

The entire contents of the various patents and other publications referred to in this specification are incorporated herein by reference

What is claimed is:

1. A photographic element comprising a light-sensitive silver halide emulsion layer having associated therewith a cyan coupler having formula (I);

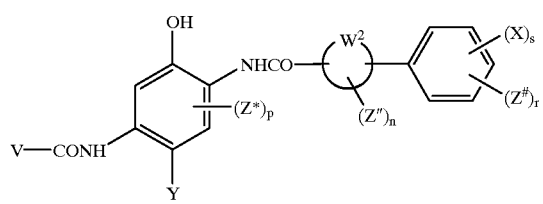

(I)

wherein:

V is a sulfone or sulfoxide containing group;

Y is H or a coupling-off group;

$W^2$ represents the atoms necessary to complete a carbocyclic or heterocyclic ring group;

each $Z''$, $Z^*$ and $Z^\#$ is an independently selected substituent group where n and r are independently 0 to 4 and p is 0 to 2; and X is a halogen atom, and s is 1 to 5;

provided that the combined sum of the aliphatic carbon atoms in V, all $Z''$, all $Z^\#$, and all $Z^*$ is at least 8.

2. The element of claim 1 wherein the coupler is represented by formula (II):

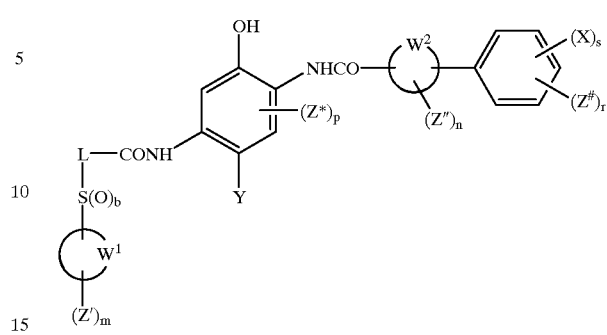

wherein:

L is a linking group;

b is 1 or 2;

$W^1$ represents the atoms necessary to complete a heterocyclic or carbocyclic ring group;

each $Z'$ is an independently selected substituent group where m is 0 to 4;

Y, $Z^*$, p, $W^2$, $Z''$, n, X, s, $Z^\#$, and r are as defined in claim 1;

provided that the combined sum of the aliphatic carbon atoms in L, all $Z'$, all $Z''$ and all $Z^*$ is at least 8.

3. The element of claim 2 wherein the coupler is represented by formula (III):

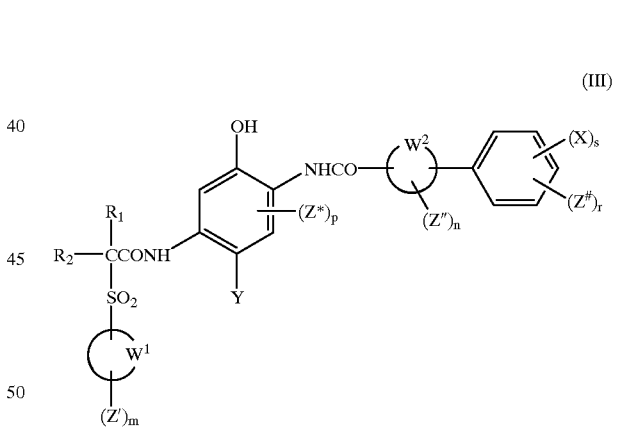

wherein:

$R_1$ and $R_2$ are independently H or an alkyl group of 1 to 5 carbon atoms;

$W^1$, $Z'$, m, Y, $Z^*$, p, $W^2$, $Z''$, n, X, s, $Z^\#$, and r are as defined in claim 2;

provided that the combined sum of the aliphatic carbon atoms in $R_1$, $R_2$, all $Z'$, all $Z''$, all $Z^\#$, and all $Z^*$ is at least 8.

4. The element of claim 3 wherein the coupler is represented by formula (IV):

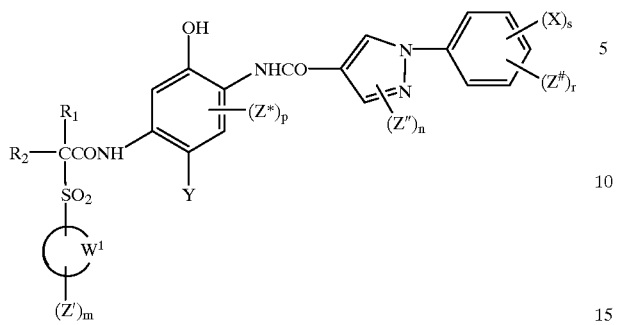

wherein n is 0 to 2.

5. The element of claim 1 wherein at least one X is chloro.

6. The element of claim 5 wherein s is at least two and at least two X are chloro.

7. The element of claim 6 wherein said two chloro groups are in the meta- or para-position to the ring formed by $W^2$.

8. The element of claim 4 wherein s is at least 1 and at least one X is chloro.

9. The element of claim 8 wherein s is at least two and at least two X are chloro.

10. The element of claim 9 wherein said two chloro groups are in the meta- or para-position to the ring formed by $W^2$.

11. The element of claim 2 wherein $W^1$ or $W^2$ is a heterocycle selected from the group consisting of benzimidazolyl, benzoselenazolyl, benzothiazolyl, benzoxazolyl, chromonyl, furyl, imidazolyl, indazolyl, indolyl, isoquinolyl, isothiazolyl, isoxazolyl, morpholinyl, oxadiazolyl, oxazolyl, picolinyl, piperidinyl, purinyl, pyradazinyl, pyranyl, pyrazinyl, pyrazolyl, pyridyl, pyrimidinyl, pyrrolyl, pyrrolidinyl, quinaldinyl, quinazolinyl, quinolyl, quinoxalinyl, selenazoyl, tellurazolyl, tetrazolyl, tetrahydrofuryl, thiadiazolyl, thiamorpholinyl, thiatriazolyl, thiazolyl, thienyl, thiophenyl, and triazolyl groups..

12. The element of claim 3 wherein each Z', Z'', and Z* is independently selected from acyl, acyloxy, alkenyl, alkyl, alkoxy, aryl, aryloxy, carbamoyl, carbonamido, carboxy, cyano, halogen, heterocyclic, hydroxy, nitro, oxycarbonyl, oxysulfonyl, sulfamoyl, sulfonamido, sulfonyl, sulfoxide, thio, and ureido groups.

13. The element of claim 12 wherein each $Z^\#$ is selected from the group consisting of acyl, acyloxy, alkenyl, alkyl, alkoxy, aryl, aryloxy, carbamoyl, carbonamido, carboxy, cyano, heterocyclic, hydroxy, nitro, oxysulfonyl, sulfamoyl, sulfonamido, sulfonyl, sulfoxide, thio, and ureido groups.

14. The element of claim 3 wherein $R_1$ or $R_2$ is an alkyl group.

15. The element of claim 2 wherein at least one Z', $Z^\#$, or Z'' is present as an alkyl or alkoxy group.

16. The element of claim 2 wherein $W^1$ represents the atoms necessary to form a phenyl ring group.

17. A photographic element in accordance with claim 1 wherein the photographic coupler is selected from the following.

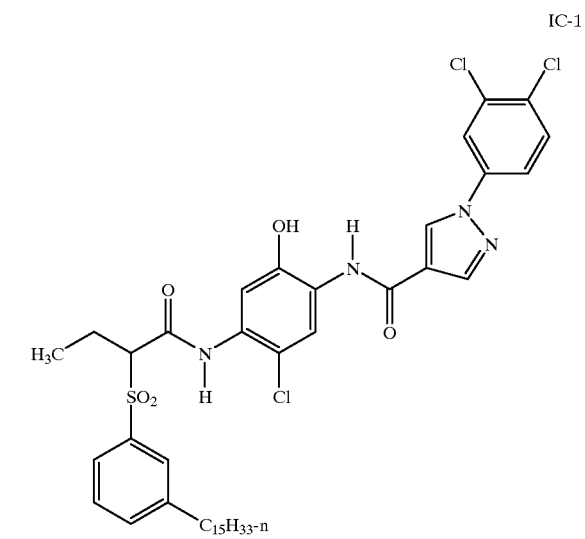

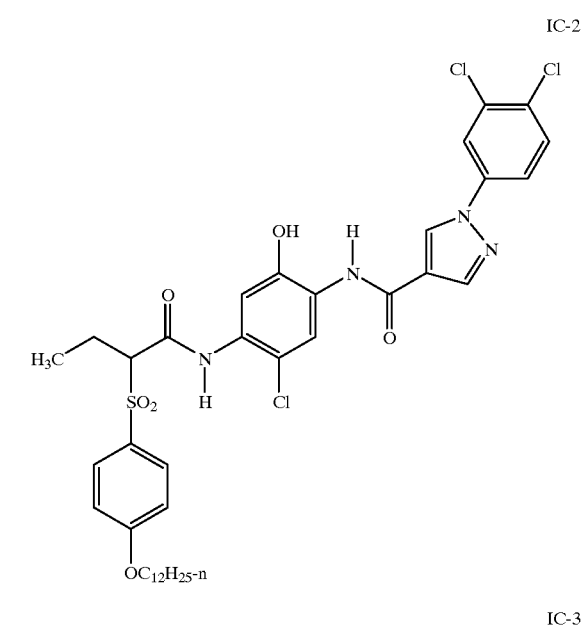

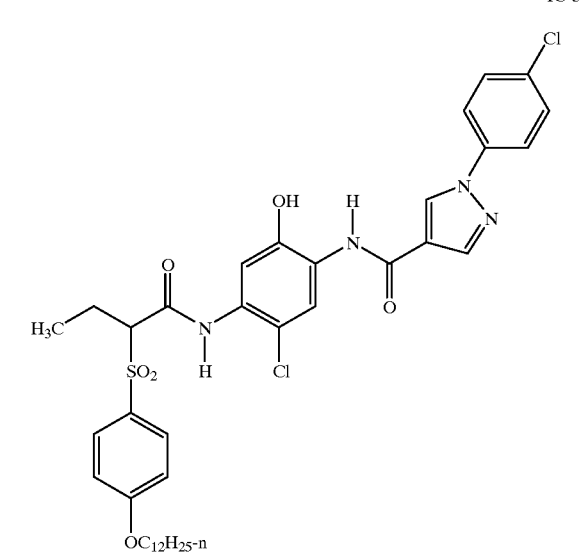

IC-4
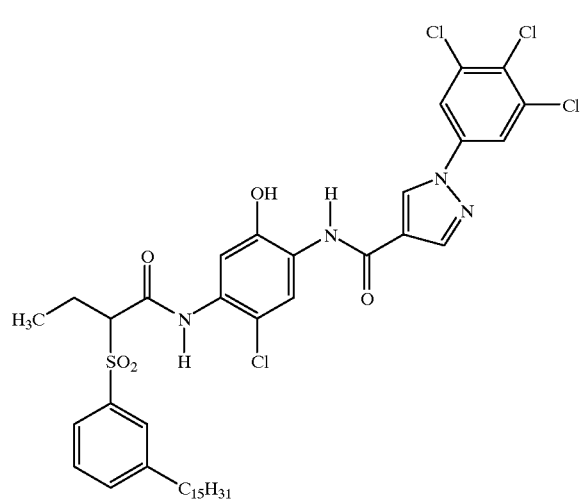
IC-5
IC-6
IC-7
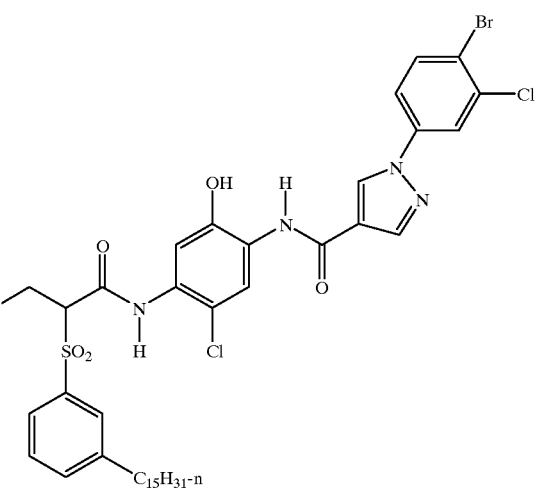
IC-8
IC-9
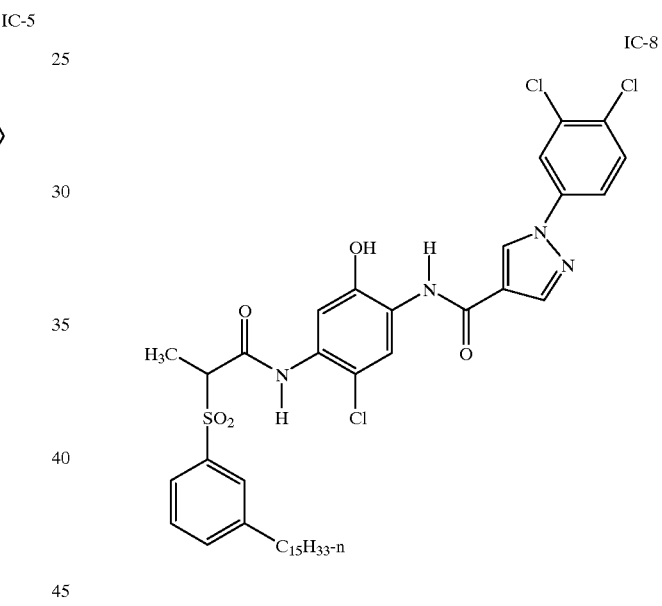
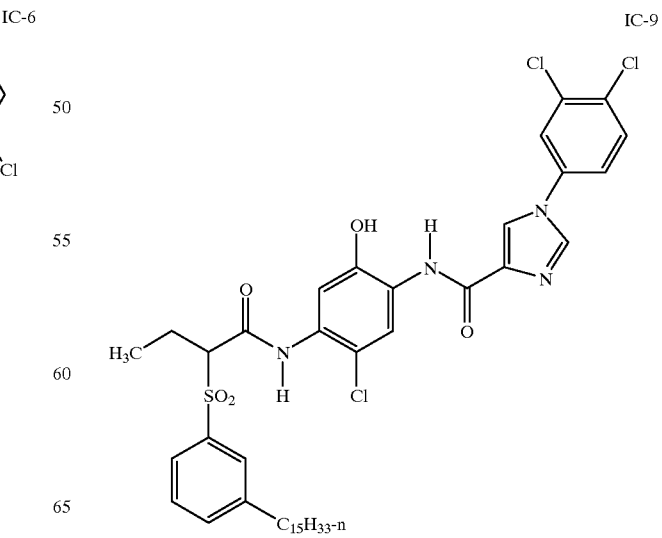

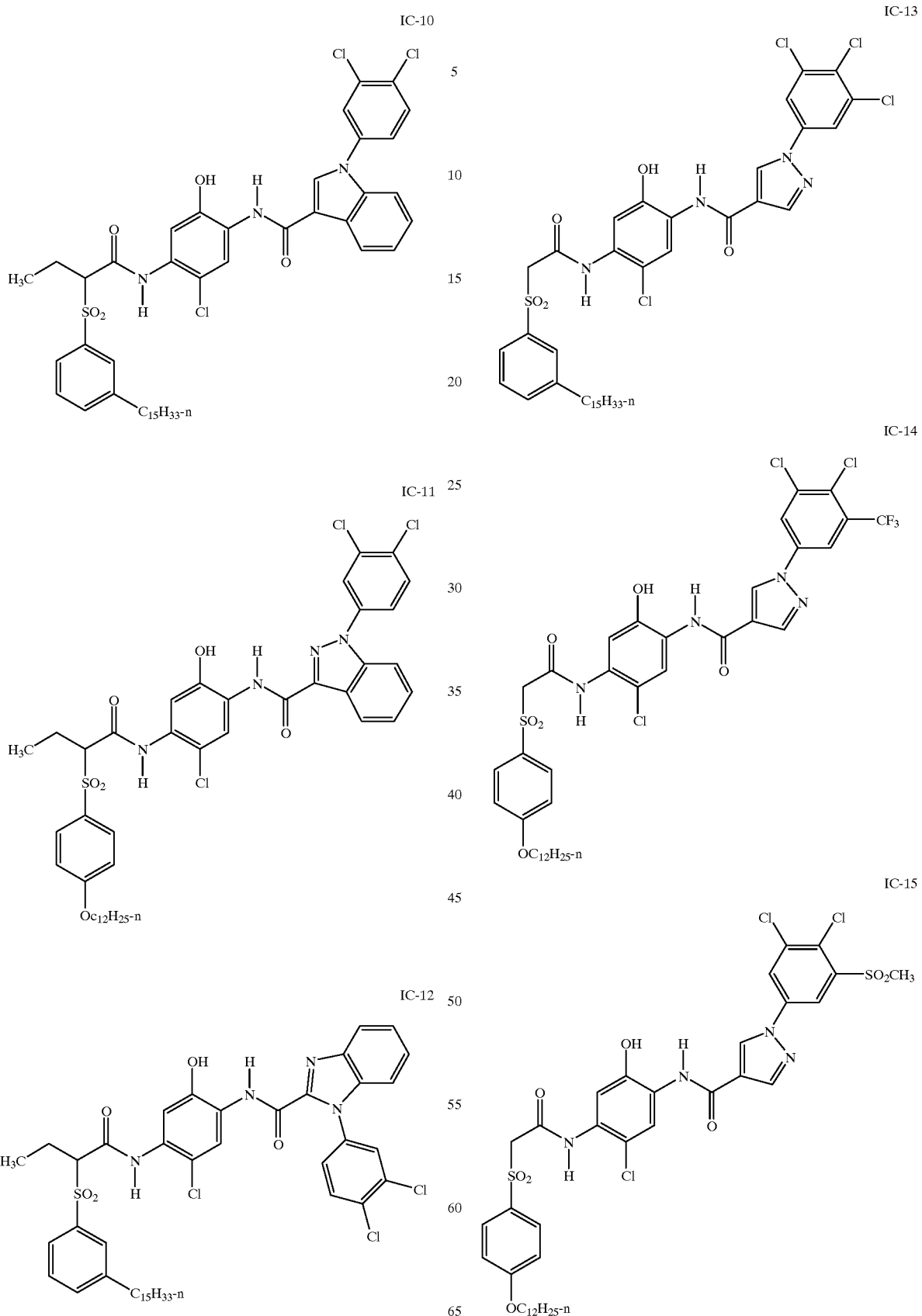

IC-16

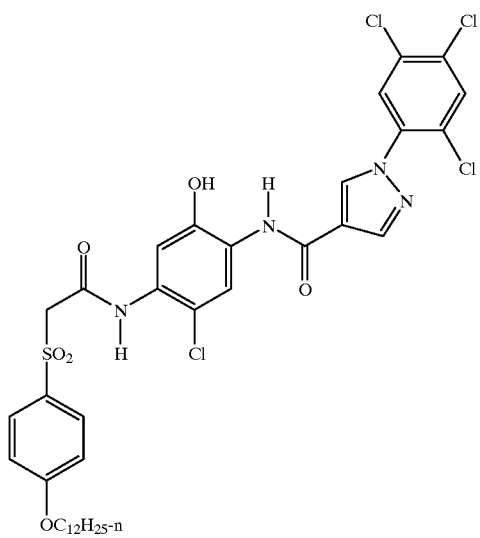

IC-17

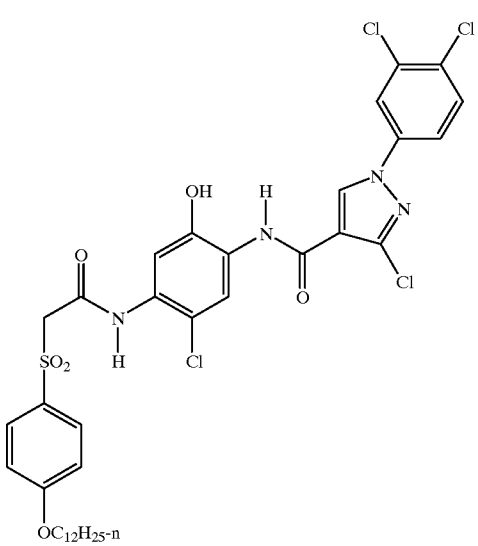

IC-18

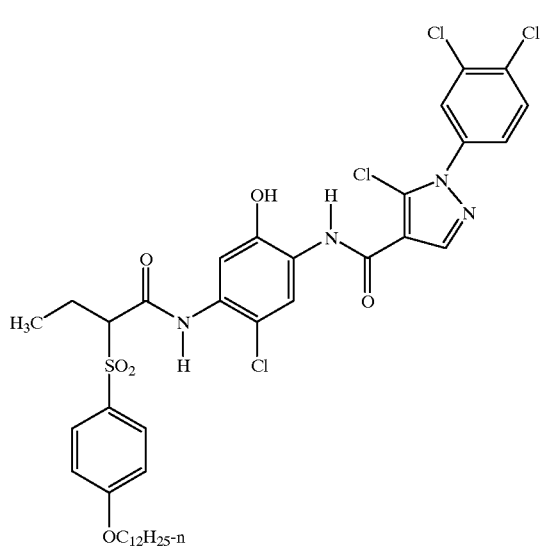

IC-19

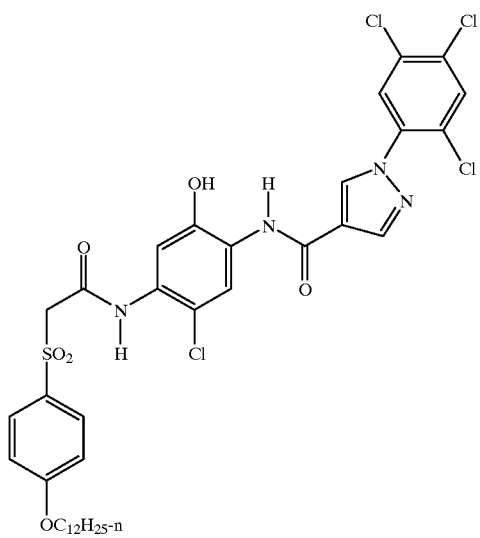

IC-20

18. The element of claim 1 provided on a reflective support.

19. The element of claim 1 packaged with instruction to process using a color negative print developing process.

20. The element of claim 1 packaged with instructions to process using a color reversal developing process.

21. The element of claim 1 wherein the element is a direct-view element.

22. A process for forming an image in an element as described in claim 1 after the element has been imagewise exposed to light comprising contacting the element with a color-developing compound.

23. The process of claim 22 in which the developer is a p-phenylene diamine compound.

* * * * *